(12) United States Patent
Chiu et al.

(10) Patent No.: US 11,058,856 B2
(45) Date of Patent: Jul. 13, 2021

(54) SYSTEMS, DEVICES AND METHODS FOR DISPENSING ORAL TRANSMUCOSAL DOSAGE FORMS

(71) Applicant: AcelRx Pharmaceuticals, Inc., Redwood City, CA (US)

(72) Inventors: Edmond Chiu, San Francisco, CA (US); Casidy Domingo, San Mateo, CA (US)

(73) Assignee: AcelRx Pharmaceuticals, Inc., Redwood City, CA (US)

( * ) Notice: Subject to any disclaimer, the term of this patent is extended or adjusted under 35 U.S.C. 154(b) by 715 days.

(21) Appl. No.: 14/978,634

(22) Filed: Dec. 22, 2015

(65) Prior Publication Data
US 2016/0175533 A1    Jun. 23, 2016

Related U.S. Application Data

(60) Provisional application No. 62/096,124, filed on Dec. 23, 2014.

(51) Int. Cl.
*A61M 37/00* (2006.01)

(52) U.S. Cl.
CPC .............................. *A61M 37/0069* (2013.01)

(58) Field of Classification Search
CPC . A61M 37/0069; A61M 25/0023; A61D 7/00; A61K 9/0024; A61B 2090/3987
See application file for complete search history.

(56) References Cited

U.S. PATENT DOCUMENTS

| | | | |
|---|---|---|---|
| 2,621,655 A | 12/1952 | Olson et al. |
| 3,162,322 A | 12/1964 | Gilbertson |
| 3,238,941 A | 3/1966 | Klein et al. |
| 3,444,858 A | 5/1969 | Russell |
| 3,757,781 A | 9/1973 | Smart |
| 3,780,735 A | 12/1973 | Crouter et al. |
| 3,789,845 A | 2/1974 | Long |

(Continued)

FOREIGN PATENT DOCUMENTS

| | | |
|---|---|---|
| CN | 2776369 | 5/2006 |
| CN | 203898925 U | 10/2014 |

(Continued)

OTHER PUBLICATIONS

Office Action for U.S. Appl. No. 15/292,909, dated Mar. 31, 2017, 6 pages.
(Continued)

*Primary Examiner* — Amber R Stiles
*Assistant Examiner* — Alexandra Lalonde
(74) *Attorney, Agent, or Firm* — Cooley LLP

(57) ABSTRACT

An apparatus includes a housing and a pushrod. The housing defines a delivery passage and an exit port in fluid communication with the delivery passage. At least a portion of the pushrod is movably disposed in the delivery passage. A distal end portion of the pushrod is configured to move a drug dosage form through at least a portion of the delivery passage to convey the drug dosage form through the exit port when the distal end portion of the pushrod is moved from a first position to a second position. A surface of at least one of the pushrod or the housing defining the delivery passage is nonplanar, curved and/or contoured.

26 Claims, 12 Drawing Sheets

(56) References Cited

U.S. PATENT DOCUMENTS

| | | |
|---|---|---|
| 4,020,558 A | 5/1977 | Cournut et al. |
| 4,060,083 A | 11/1977 | Hanson |
| 4,226,848 A | 10/1980 | Nagai et al. |
| 4,237,884 A | 12/1980 | Erikson |
| 4,465,191 A | 8/1984 | Darbo |
| 4,474,308 A | 10/1984 | Bergeron |
| 4,489,853 A | 12/1984 | Korte et al. |
| 4,657,533 A * | 4/1987 | Oscarsson ......... A61M 37/0069 604/60 |
| 4,671,953 A | 6/1987 | Stanley et al. |
| 4,733,797 A | 3/1988 | Haber |
| 4,764,378 A | 8/1988 | Keith et al. |
| 4,769,011 A | 9/1988 | Swaniger |
| 4,782,981 A | 11/1988 | Schuster |
| 4,785,969 A | 11/1988 | McLaughlin |
| 4,863,737 A | 9/1989 | Stanley et al. |
| 4,950,234 A | 8/1990 | Fujioka et al. |
| 5,122,127 A | 6/1992 | Stanley |
| 5,190,185 A | 3/1993 | Blechl |
| 5,263,596 A | 11/1993 | Williams |
| 5,292,307 A | 3/1994 | Dolzine et al. |
| 5,296,234 A | 3/1994 | Hadaway et al. |
| 5,344,043 A | 9/1994 | Moulding et al. |
| 5,348,158 A | 9/1994 | Honan et al. |
| 5,366,112 A | 11/1994 | Hinterreiter |
| 5,366,113 A | 11/1994 | Kim et al. |
| 5,489,025 A | 2/1996 | Romick |
| 5,507,277 A | 4/1996 | Rubsamen et al. |
| 5,507,807 A | 4/1996 | Shippert |
| 5,540,665 A | 7/1996 | Mercado et al. |
| 5,549,560 A | 8/1996 | Van de Wijdeven |
| 5,584,805 A | 12/1996 | Sutton |
| 5,646,912 A | 7/1997 | Cousin |
| 5,657,748 A | 8/1997 | Braithwaite |
| 5,660,273 A | 8/1997 | Discko, Jr. |
| 5,694,919 A | 12/1997 | Rubsamen et al. |
| 5,710,551 A | 1/1998 | Ridgeway |
| 5,724,957 A | 3/1998 | Rubsamen et al. |
| 5,735,263 A | 4/1998 | Rubsamen et al. |
| 5,752,620 A | 5/1998 | Pearson |
| 5,762,631 A | 6/1998 | Klein |
| 5,850,937 A | 12/1998 | Rauche |
| 5,860,946 A | 1/1999 | Hofstatter |
| 5,945,651 A | 8/1999 | Chorosinski et al. |
| 5,950,632 A | 9/1999 | Reber et al. |
| 5,954,641 A | 9/1999 | Kehr et al. |
| 5,968,547 A | 10/1999 | Reder et al. |
| 5,984,888 A | 11/1999 | Nielsen et al. |
| 5,992,742 A | 11/1999 | Sullivan et al. |
| 5,995,938 A | 11/1999 | Whaley |
| 5,997,518 A | 12/1999 | Laibovitz et al. |
| 6,010,483 A | 1/2000 | Spencer |
| 6,039,251 A | 3/2000 | Holowko et al. |
| 6,116,414 A | 9/2000 | Discko, Jr. |
| 6,131,765 A | 10/2000 | Barry et al. |
| 6,171,294 B1 | 1/2001 | Southam et al. |
| 6,190,326 B1 | 2/2001 | McKinnon et al. |
| 6,200,288 B1 | 3/2001 | Heaton et al. |
| 6,216,033 B1 | 4/2001 | Southam et al. |
| 6,224,908 B1 | 5/2001 | Wong et al. |
| 6,230,927 B1 | 5/2001 | Schoonen et al. |
| 6,234,343 B1 | 5/2001 | Papp |
| 6,251,418 B1 | 6/2001 | Ahern et al. |
| 6,258,056 B1 | 7/2001 | Turley et al. |
| 6,264,981 B1 | 7/2001 | Zhang et al. |
| 6,294,999 B1 | 9/2001 | Yarin et al. |
| 6,310,072 B1 | 10/2001 | Smith et al. |
| 6,319,510 B1 | 11/2001 | Yates |
| 6,328,159 B1 | 12/2001 | Discko, Jr. |
| 6,350,470 B1 | 2/2002 | Pather et al. |
| 6,364,158 B1 | 4/2002 | Dimoulis |
| 6,425,495 B1 | 7/2002 | Senda et al. |
| 6,425,892 B2 | 7/2002 | Southam et al. |
| 6,484,718 B1 | 11/2002 | Schaeffer et al. |
| 6,488,953 B2 | 12/2002 | Halliday et al. |
| 6,495,120 B2 | 12/2002 | McCoy et al. |
| 6,529,446 B1 | 3/2003 | de la Huerga |
| 6,541,021 B1 | 4/2003 | Johnson et al. |
| 6,564,967 B1 | 5/2003 | Stringfield et al. |
| 6,572,891 B1 | 6/2003 | Ugarkovic |
| 6,605,060 B1 | 8/2003 | O'Neil |
| 6,651,651 B1 | 11/2003 | Bonney et al. |
| 6,660,295 B2 | 12/2003 | Watanabe et al. |
| 6,682,716 B2 | 1/2004 | Hodges et al. |
| 6,685,951 B2 | 2/2004 | Cutler et al. |
| 6,689,373 B2 | 2/2004 | Johnson et al. |
| 6,726,053 B1 | 4/2004 | Harrold |
| 6,752,145 B1 | 6/2004 | Bonney et al. |
| 6,761,910 B1 | 7/2004 | Pettersson et al. |
| 6,762,684 B1 | 7/2004 | Camhi et al. |
| 6,776,978 B2 | 8/2004 | Rabinowitz et al. |
| 6,793,075 B1 | 9/2004 | Jeter |
| 6,796,429 B2 | 9/2004 | Cameron et al. |
| 6,824,512 B2 | 11/2004 | Warkentin et al. |
| 6,835,194 B2 | 12/2004 | Johnson et al. |
| 6,855,310 B2 | 2/2005 | Rabinowitz et al. |
| 6,881,208 B1 | 4/2005 | Phipps et al. |
| 6,914,668 B2 | 7/2005 | Brestel et al. |
| 6,959,808 B2 | 11/2005 | Discko, Jr. |
| 7,004,111 B2 | 2/2006 | Olson et al. |
| 7,018,370 B2 | 3/2006 | Southam et al. |
| 7,018,619 B2 | 3/2006 | Rabinowitz et al. |
| 7,044,125 B2 | 5/2006 | Vedrine et al. |
| 7,044,302 B2 | 5/2006 | Conley et al. |
| 7,070,762 B2 | 7/2006 | Rabinowitz et al. |
| 7,070,764 B2 | 7/2006 | Rabinowitz et al. |
| 7,070,765 B2 | 7/2006 | Rabinowitz et al. |
| 7,072,738 B2 | 7/2006 | Bonney et al. |
| 7,073,685 B1 | 7/2006 | Giraud et al. |
| 7,078,018 B2 | 7/2006 | Rabinowitz et al. |
| 7,078,019 B2 | 7/2006 | Rabinowitz et al. |
| 7,090,830 B2 | 8/2006 | Hale |
| 7,118,550 B2 | 10/2006 | Loomis |
| 7,119,690 B2 | 10/2006 | Lerch et al. |
| 7,169,378 B2 | 1/2007 | Rabinowitz et al. |
| 7,172,573 B1 | 2/2007 | Lamb |
| 7,198,172 B2 | 4/2007 | Harvey et al. |
| 7,264,139 B2 | 9/2007 | Brickwood et al. |
| 7,458,374 B2 | 12/2008 | Hale et al. |
| 7,468,179 B2 | 12/2008 | Rabinowitz et al. |
| 7,484,642 B2 | 2/2009 | Bonney |
| 7,500,444 B2 | 3/2009 | Bonney et al. |
| 7,540,998 B2 | 6/2009 | Terwilliger et al. |
| 7,552,728 B2 | 6/2009 | Bonney et al. |
| 7,581,657 B2 | 9/2009 | Dickmann |
| 7,743,923 B2 | 6/2010 | Conley |
| 7,744,558 B2 | 6/2010 | Maag |
| 7,896,192 B2 | 3/2011 | Conley et al. |
| 8,062,248 B2 | 11/2011 | Kindel |
| 8,142,733 B2 | 3/2012 | Creaven |
| 8,357,114 B2 | 1/2013 | Poutiatine et al. |
| 8,499,966 B2 | 8/2013 | Palmer et al. |
| 8,548,623 B2 | 10/2013 | Poutiatine et al. |
| 8,574,189 B2 | 11/2013 | Poutiatine et al. |
| 8,706,288 B2 | 4/2014 | Alpay |
| 8,753,308 B2 | 6/2014 | Palmer et al. |
| 8,778,393 B2 | 7/2014 | Palmer et al. |
| 8,778,394 B2 | 7/2014 | Palmer et al. |
| 8,865,211 B2 | 10/2014 | Tzannis et al. |
| 8,865,743 B2 | 10/2014 | Palmer |
| 8,905,964 B2 | 12/2014 | Poutiatine et al. |
| 8,945,592 B2 | 2/2015 | Pushpala et al. |
| 9,066,847 B2 | 6/2015 | Poutiatine et al. |
| 9,289,583 B2 | 3/2016 | Palmer et al. |
| 9,320,710 B2 | 4/2016 | Palmer et al. |
| 9,642,996 B2 | 5/2017 | Palmer et al. |
| 2001/0020147 A1 | 9/2001 | Staniforth et al. |
| 2002/0026330 A1 | 2/2002 | Klein |
| 2002/0071857 A1 | 6/2002 | Kararli et al. |
| 2002/0110578 A1 | 8/2002 | Pather et al. |
| 2002/0142050 A1 | 10/2002 | Straub et al. |
| 2002/0160043 A1 | 10/2002 | Coleman |
| 2003/0008005 A1 | 1/2003 | Cutler |
| 2003/0015196 A1 | 1/2003 | Hodges et al. |

(56) References Cited

U.S. PATENT DOCUMENTS

| | | |
|---|---|---|
| 2003/0015197 A1 | 1/2003 | Hale et al. |
| 2003/0017175 A1 | 1/2003 | Cutler |
| 2003/0022910 A1 | 1/2003 | Cutler |
| 2003/0052135 A1 | 3/2003 | Conley et al. |
| 2003/0052787 A1 | 3/2003 | Zerhusen et al. |
| 2003/0077300 A1 | 4/2003 | Wermeling et al. |
| 2003/0099158 A1 | 5/2003 | De La Huerga |
| 2003/0130314 A1 | 7/2003 | Druzgala |
| 2003/0132239 A1 | 7/2003 | Konig et al. |
| 2003/0173408 A1 | 9/2003 | Mosher et al. |
| 2003/0185872 A1 | 10/2003 | Kochinke |
| 2003/0190290 A1 | 10/2003 | Ross |
| 2003/0225367 A1* | 12/2003 | Sabra ............ A61M 37/0069 604/63 |
| 2003/0232080 A1 | 12/2003 | Pather et al. |
| 2004/0017567 A1 | 1/2004 | Loicht et al. |
| 2004/0025871 A1 | 2/2004 | Davies |
| 2004/0034059 A1 | 2/2004 | Grarup et al. |
| 2004/0037882 A1 | 2/2004 | Johnson et al. |
| 2004/0080515 A1 | 4/2004 | Hagiwara |
| 2004/0092531 A1 | 5/2004 | Chizh et al. |
| 2004/0094564 A1 | 5/2004 | Papp |
| 2004/0111053 A1 | 6/2004 | Nicolette |
| 2004/0120896 A1 | 6/2004 | Dugger |
| 2004/0133305 A1 | 7/2004 | Jean-Pierre |
| 2004/0158349 A1 | 8/2004 | Bonney et al. |
| 2004/0170567 A1 | 9/2004 | Sackler |
| 2004/0180080 A1 | 9/2004 | Furusawa et al. |
| 2004/0248964 A1 | 12/2004 | Crooks et al. |
| 2004/0253307 A1 | 12/2004 | Hague et al. |
| 2005/0038062 A1 | 2/2005 | Burns et al. |
| 2005/0049464 A1 | 3/2005 | Lassers et al. |
| 2005/0054942 A1 | 3/2005 | Melker |
| 2005/0065175 A1 | 3/2005 | Gonzales et al. |
| 2005/0089479 A1 | 4/2005 | Rabinowitz et al. |
| 2005/0101936 A1 | 5/2005 | Gonzales et al. |
| 2005/0122219 A1 | 6/2005 | Petersen et al. |
| 2005/0131386 A1 | 6/2005 | Freeman et al. |
| 2005/0142197 A1 | 6/2005 | Moe et al. |
| 2005/0142198 A1 | 6/2005 | Moe et al. |
| 2005/0150488 A1 | 7/2005 | Dave |
| 2005/0150489 A1 | 7/2005 | Dunfield et al. |
| 2005/0163838 A1 | 7/2005 | Moe |
| 2005/0169989 A1 | 8/2005 | Moe et al. |
| 2005/0176790 A1 | 8/2005 | Bartholomaus |
| 2005/0177275 A1 | 8/2005 | Harvey et al. |
| 2006/0026035 A1 | 2/2006 | Younkes et al. |
| 2006/0028727 A1 | 2/2006 | Moon et al. |
| 2006/0031099 A1 | 2/2006 | Vitello et al. |
| 2006/0039959 A1 | 2/2006 | Wessling et al. |
| 2006/0045865 A1 | 3/2006 | Jacob et al. |
| 2006/0062812 A1 | 3/2006 | Ross et al. |
| 2006/0067978 A1 | 3/2006 | Heiler et al. |
| 2006/0089858 A1 | 4/2006 | Ling |
| 2006/0134200 A1 | 6/2006 | Vandoni et al. |
| 2006/0216352 A1 | 9/2006 | Nystrom et al. |
| 2006/0229570 A1 | 10/2006 | Lovell et al. |
| 2006/0247578 A1 | 11/2006 | Arguedas et al. |
| 2006/0259188 A1 | 11/2006 | Berg |
| 2007/0005005 A1* | 1/2007 | Wang ............ A61M 37/0069 604/60 |
| 2007/0020186 A1 | 1/2007 | Stroppolo et al. |
| 2007/0036853 A1 | 2/2007 | Agarwal et al. |
| 2007/0071806 A1 | 3/2007 | McCarty |
| 2007/0074722 A1 | 4/2007 | Giroux et al. |
| 2007/0104763 A1 | 5/2007 | Jobdevairakkam et al. |
| 2007/0185084 A1 | 8/2007 | McKinney et al. |
| 2007/0190130 A1 | 8/2007 | Mark et al. |
| 2007/0207207 A1 | 9/2007 | Tzannis et al. |
| 2007/0260491 A1 | 11/2007 | Palmer et al. |
| 2007/0286900 A1 | 12/2007 | Herry et al. |
| 2007/0299687 A1 | 12/2007 | Palmer et al. |
| 2008/0166404 A1 | 7/2008 | Tzannis et al. |
| 2008/0203107 A1 | 8/2008 | Conley et al. |
| 2008/0268023 A1 | 10/2008 | Palmer et al. |
| 2009/0010992 A1 | 1/2009 | Palmer et al. |
| 2009/0048237 A1 | 2/2009 | Palmer et al. |
| 2009/0131479 A1 | 5/2009 | Palmer et al. |
| 2009/0294521 A1 | 12/2009 | de la Huerga |
| 2010/0105735 A1 | 4/2010 | Palmer et al. |
| 2010/0130551 A1 | 5/2010 | Pushpala et al. |
| 2010/0256190 A1 | 10/2010 | Palmer et al. |
| 2010/0331874 A1* | 12/2010 | Bardy ............ A61M 37/0069 606/185 |
| 2011/0091544 A1 | 4/2011 | Palmer |
| 2011/0098595 A1* | 4/2011 | Hibner ............ A61B 17/3468 600/562 |
| 2011/0208118 A1 | 8/2011 | Katz |
| 2011/0288128 A1 | 11/2011 | Palmer et al. |
| 2012/0035216 A1 | 2/2012 | Palmer et al. |
| 2013/0090594 A1* | 4/2013 | Palmer ............ A61J 7/0053 604/60 |
| 2013/0158074 A1 | 6/2013 | Palmer et al. |
| 2013/0165481 A1 | 6/2013 | Palmer et al. |
| 2014/0031975 A1 | 1/2014 | Poutiatine et al. |
| 2014/0350054 A1 | 11/2014 | Palmer et al. |
| 2015/0038898 A1 | 2/2015 | Palmer et al. |
| 2015/0105424 A1 | 4/2015 | Palmer et al. |
| 2016/0213606 A1 | 7/2016 | Palmer et al. |
| 2017/0259051 A1 | 9/2017 | Palmer et al. |

FOREIGN PATENT DOCUMENTS

| | | |
|---|---|---|
| EP | 1648327 A2 | 4/2006 |
| EP | 1261316 B1 | 4/2008 |
| EP | 1968539 | 9/2008 |
| EP | 1257311 B1 | 12/2008 |
| EP | 2114383 B1 | 7/2010 |
| GB | 2309966 | 8/1997 |
| JP | 2000-53174 | 2/2000 |
| JP | 2000-142841 | 5/2000 |
| JP | 2000-511158 | 8/2000 |
| JP | 2003-525081 | 8/2003 |
| JP | 2007-517636 | 7/2007 |
| WO | WO 00/66458 | 11/2000 |
| WO | WO 01/97780 | 12/2001 |
| WO | WO 02/32487 | 4/2002 |
| WO | WO 02/74372 | 9/2002 |
| WO | WO 02/78594 | 10/2002 |
| WO | WO 03/70304 | 8/2003 |
| WO | WO 03/92575 | 11/2003 |
| WO | WO 2004/067004 | 8/2004 |
| WO | WO 2004/080515 | 9/2004 |
| WO | WO 2008/085764 | 7/2008 |
| WO | WO 2008/085765 | 7/2008 |
| WO | WO 2016/106329 A1 | 6/2016 |

OTHER PUBLICATIONS

Extended European Search Report for European Application No. 17178215.4, dated Dec. 11, 2017, 8 pages.

Examination Report for Indian Patent Application No. 2873/KOLNP/2008, dated Mar. 7, 2017, 6 pages.

Hearing Notice for Indian Patent Application No. 2873/KOLNP/2008, mailed on Jul. 26, 2018, 3 pages.

Office Action for Indian Application No. 2438/KOLNP/2009, dated Sep. 5, 2017, 6 pages.

Office Action for European Application No. 13161632.8, dated Mar. 28, 2017, 5 pages.

Written Opinion for Singapore Application No. 11201704797T, dated Feb. 12, 2018, 5 pages.

Office Action for U.S. Appl. No. 15/589,607, dated Nov. 8, 2018, 12 pages.

Abrams, R. et al., "Safety and effectiveness of intranasal administration of sedative medications (ketamine, midazolam, or sufentanil) for urgent brief pediatric dental procedures," Anesth. Prog., 40:63-66 (1993).

AcelRx Pharmaceuticals, Inc., "AcelRx Pharmaceuticals Reports Positive Results from a Clinical Trial of Sublingual Sufentanil/Triazolam NanoTabTM Combination (ARX-03) in Treating Procedural Pain and Anxiety," Jan. 12, 2009, pp. 1-2.

(56) References Cited

OTHER PUBLICATIONS

ACTIQ® Fact Sheet (Mar. 2004).
Albert, J. M. et al., "Patient-controlled analgesia vs. conventional intramuscular analgesia following colon surgery," Diseases of the Colon & Rectum, 31(2):83-86 (1988).
Bredenberg, S., "New concepts in administration of drugs in tablet form—Formulation and evaluation of a sublingual tablet for rapid absorption, and presentation of an individualised dose administration system," Comprehensive Summaries of Uppsala Dissertations from the Faculty of Pharmacy 287, ACTA Universitatis Upsaliensis Uppsala (2003).
Bredenberg, S. et al., "In vitro and in vivo evaluation of a new sublingual tablet system for rapid oromucosal absorption using fentanyl citrate as the active substance," European Journal of Pharmaceutical Sciences, 20:327-334 (2003).
Chelly, J. E. et al., "The safety and efficacy of a fentanyl patient-controlled transdermal system for acute postoperative analgesia: a multicenter, placebo-controlled trial," Anesth. Analg., 98:427-433 (2004).
Christie, J. M. et al., "Dose-titration, multi-center study of oral transmucosal fentanyl citrate for the treatment of breakthrough pain in cancer patients using transdermal fentanyl for persistent pain," J Clin Oncol., 16(10):3238-45 (1998).
Coda, B. A. et al., "Comparative efficacy of patient-controlled administration of morphine, hydromorphone, or sufentanil for the treatment of oral mucositis pain following bone marrow transplantation," Pain, 72:333-346 (1997).
Collins, L. M. C. et al., "The surface area of the adult human mouth and thickness of the salivary film covering the teeth and oral mucosa," J. Dent. Res., 66(8):1300-1302 (1987).
Culling et al., "Haemodynamics and plasma concentrations following sublingual GTN and intravenous, or inhaled isosorbide dinitrate," Br. J. Clin. Pharm., 17:125-131 (1984).
Dale, O. et al., "Nasal Administration of Opioids for Pain Management in Adults," Acta Anaesthesiol. Scand., 46:759-770 (2002).
Darwish, M. et al., "Single-Dose and Steady-State Pharmacokinetics of Fentanyl Buccal Tablet in Healthy Volunteers," Journal of Clinical Pharmacology, 47(1):56-63 (2007).
Darwish, M. et al., "Pharmacokinetics and dose proportionality of fentanyl effervescent buccal tablets in healthy volunteers," Clinical Pharmacokinetics, 44(12):1279-1286 (2005).
Darwish, M. et al., "Comparison of equivalent doses of fentanyl buccal tablets and arteriovenous differences in fentanyl pharmacokinetics," Clinical Pharmacokinetics, 45(8):843-850 (2006).
Darwish, M. et al., "Pharmacokinetic properties of fentanyl effervescent buccal tablets: a phase I, open-label, crossover study of single-dose 100, 200, 400, and 800 μg in healthy adult volunteers," Clinical Therapeutics, 28(5):707-714 (2006).
Darwish, M. et al., "Relative bioavailability of the fentanyl effervescent buccal tablet (FEBT) 1080 μg versus oral transmucosal fentanyl citrate 1600 μg and dose proportionality of FEBT 270 to 1300 μg: a single-dose, randomized, open-label, three-period study in healthy adult volunteers," Clinical Therapeutics, 28(5):715-724.
Darwish, M. et al., "Effect of buccal dwell time on the pharmacokinetic profile of fentanyl buccal tablet," Expert Opin. Pharmacother., 8(13):2011-2016 (2007).
Darwish, M. et al., "Bioequivalence following buccal and sublingual placement of fentanyl buccal tablet 400 μg in healthy subjects," Clin. Drug Invest., 28(1):1-7 (2008).
Darwish, M. et al., "Absolute and Relative Bioavailability of Fentanyl Buccal Tablet and Oral Transmucosal Fentanyl Citrate," Journal of Clinical Pharmacology, 47:343-350 (2007).
De Vries, M. E. et al., "Developments in buccal drug delivery," Critical Reviews in Therapeutic Drug Carrier Systems, 8(3):271-303 (1991).
Drug Information Bulletin [online], 37(4) (Sep./Oct. 2004), [Retrieved on Jun. 5, 2008.] Retrieved from the Internet: <URL: http://www.kgh.on.ca/pharmacy/diBulletinSeptOct2004.pdf>, 4 pages.

Enting, R. H. et al., "The 'pain pen' for breakthrough cancer pain: a promising treatment," Journal of Pain and Symptom Management, 29(2):213-217 (2005).
FDA Guidance for Industry: Container Closure Systems for Packaging Human Drugs and Biologics, pp. 1-E2 (1999).
Fentora™ Package Insert (2006).
Fentora®, 2008 Red Book, p. 174.
Fisher, D. M. et al., "Pharmacokinetics of an implanted osmotic pump delivering sufentanil for the treatment of chronic pain," Anesthesiology, 99(4):929-937 (2003).
Gardner-Nix, J., "Oral transmucosal fentanyl and sufentanil for incident pain," Journal of Pain and Symptom Management, 22(2):627-630 (2001).
Grass, J., "Patient-controlled analgesia," Anesth. Analg., 101:S44-S61 (2005).
Griffin, D. et al., Reg. Anesth. Pain Med., vol. 10, American Society of Regional Anesthesia Spring Meeting (2010).
Hicks, R. et al., "USP Medication Safety Forum: Medication Errors Involving Patient-Controlled Analgesia," Joint Commission on Quality and Patient Safety, 34(12):734-742 (2008).
Infusion Pump Improvement Initiative, Center for Devices and Radiological Health, U.S. Food and Drug Administration, Apr. 2010, 7 pages.
Keohane, C. A. et al., "Intravenous medication safety and smart infusion systems," Journal of Infusion Nursing, 28(5):321-328 (Sep./Oct. 2005).
KGH Drug Information Bulletin, "Sublingual Sufentanil for Incident Pain," KGH Drug Information Bulletin, 37(4):2 (2004).
Kotey, G. A. et al., "Iontophoretic delivery of fentanyl for acute post-operative pain management," The European Journal of Hospital Pharmacy Science, 13(1):3-9 (2007).
Kress, J. P. et al., "Sedation and analgesia in the intensive care unit," Am. J. Respir. Crit. Care Med., 166:1024-1028 (2002).
Kunz, K. M., et al., "Severe episodic pain: management with sublingual sufentanil," Journal of Pain and Symptom Management, 8(4):189-190 (1993).
Lehmann, K. A. et al., "Postoperative patient-controlled analgesia with sufentanil: analgesic efficacy and minimum effective concentrations," Acta Anaesthesiol Scand., 35:221-226 (1991).
Lin, L. et al., "Applying human factors to the design of medical equipment: patient-controlled analgesia," J. Clin. Monitoring and Computing, 14:253-263 (1998).
Mathieu, N. et al., "Intranasal sufentanil is effective for postoperative analgesia in adults," Canadian Journal of Anesthesia, 53(1):60-66 (2006).
McInnes, F. et al., "Evaluation of the clearance of a sublinqual buprenorphine spray in the beagle dog using gamma scintigraphy," Pharmaceutical Research, (2007), 6 pages.
Miaskowski, C., "Patient-controlled modalities for acute postoperative pain management," Journal of PeriAnesthesia Nursing, 20(4):255-267 (Aug. 2005).
Miller, R. D., "The pursuit of excellence. The 47th Annual Rovenstine Lecture," Anesthesiology, 110(4):714-720 (Apr. 2009).
Momeni, M. et al., "Patient-controlled analgesia in the management of postoperative pain," Drugs, 66(18):2321-2337 (2006).
Onsolis Package Insert (Jul. 2009), 11 pages.
Rawal, N. et al., "Current practices for postoperative pain management in Europe and the potential role of the fentanyl HCl iontophoretic transdermal system," European Journal of Anaesthesiology, 24:299-308 (2007).
Reisfield, G. M. et al., "Rational use of sublingual opioids in palliative medicine," Journal of Palliative Medicine, 10(2):465-475 (2007).
Rosati, J. et al., "Evaluation of an oral patient-controlled analgesia device for pain management in oncology inpatients," J. Support. Oncol., 5(9):443-448 (2007).
Rothschild, J. M. et al., "A controlled trial of smart infusion pumps to improve medication safety in critically ill patients," Crit. Care Med., 33(3):533-540 (2005).
Shojaei, A. H. et al., "Buccal mucosa as a route for systemic drug delivery: a review," Journal of Pharmacy and Pharmaceutical Sciences, 1:15-30 (1998).

(56) References Cited

OTHER PUBLICATIONS

Siepmann, J. et al., "Calculation of the required size and shape of hydroxypropyl methylcellulose matrices to achieve desired drug release profiles," International Journal of Pharmaceutics, 201(1):151-164 (2000).
Slatkin et al., "Fentanyl Buccal Tablet for Relief of Breakthrough Pain in Opioid-Tolerant Patients With Cancer-Related Chronic Pain," J. of Supportive Oncol., vol. 5, No. 7, Jul./Aug. 2007, pp. 327-334.
Striebel, H. W. et al., "Patient-controlled intranasal analgesia (PCINA) for the management of postoperative pain: a pilot study," Journal of Clinical Anesthesia, 8:4-8 (1996).
Striebel, H. W. et al., "Patient-controlled intranasal analgesia: a method for noninvasive postoperative pain management," Anesth Analg, 83:548-551 (1996).
Sufenta® Package Insert (2006), 3 pages.
Vadivelu, N. et al., "Recent advances in postoperative pain management," Yale Journal of Biology and Medicine, 83:11-25 (2010).
Van Raders, P. et al., "Nurses' views on ease of patient care in postoperative pain management," British Journal of Nursing, 16(5):312-317 (2007).
Vercauteren, M. P. et al., "Epidural sufentanil for postoperative patient-controlled analgesia (PCA) with or without background infusion: a double-blind comparison," Anesth. Analg., 80:76-80 (1995).
Viscusi, E. R. et al., "An iontophoretic fentanyl patient-activated analgesic delivery system for postoperative pain: a double-blind, placebo-controlled trial," Anesth Analg., 102(1):188-194 (2006).
Viscusi, E. R. et al., "Patient-controlled transdermal fentanyl hydrochloride vs intravenous morphine pump for postoperative pain: a randomized controlled trial," JAMA, 291(11):1333-1341 (2004).
Viscusi, E. R., "Patient-controlled drug delivery for acute postoperative pain management: a review of current and emerging technologies," Regional Anesthesia and Pain Medicine, 33(2):146-158 (2008).
Weinberg, D. S. et al., "Sublingual absorption of selected opioid analgesics," Clin. Pharmacol. Ther., 44(3):335-342 (1988).
Zhang, H. et al., "Oral mucosal drug delivery: clinical pharmacokinetics and therapeutic applications," Clinical Pharmacokinetics, 41(9):661-680 (2002).
International Search Report and Written Opinion for International Application No. PCT/US2011/037401, dated Aug. 19, 2011.
Office Action for U.S. Appl. No. 13/416,236, dated Feb. 4, 2013.
Office Action U.S. Appl. No. 11/473,551, dated Sep. 26, 2008.
Office Action U.S. Appl. No. 11/473,551, dated Mar. 16, 2009.
Office Action U.S. Appl. No. 11/473,551, dated Sep. 11, 2009.
Office Action for U.S. Appl. No. 11/825,251, dated Aug. 5, 2010.
Office Action for Canadian Application No. 2,636,115, dated Feb. 12, 2013.
Office Action for Japanese Patent Application No. 2008-549610, dated Nov. 25, 2011.
Office Action for Japanese Patent Application No. 2008-549610, dated Nov. 15, 2012.
Office Action for U.S. Appl. No. 11/650,230, dated Sep. 25, 2008.
Office Action for U.S. Appl. No. 11/650,230, dated Mar. 10, 2009.
Office Action for U.S. Appl. No. 11/650,230, dated Aug. 4, 2009.
Office Action for U.S. Appl. No. 11/650,230, dated Feb. 2, 2010.
Office Action for U.S. Appl. No. 11/650,230, dated Jun. 16, 2010.
Office Action for U.S. Appl. No. 11/650,230, dated Mar. 1, 2011.
Office Action for U.S. Appl. No. 11/650,230, dated Mar. 27, 2012.
International Search Report and Written Opinion for International Application No. PCT/US2007/000527, dated Dec. 17, 2007.
Office Action for Canadian Application No. 2,673,880, dated May 6, 2014.
Office Action for Chinese Patent Application No. 200780051996.7, dated Feb. 23, 2012.
Office Action for U.S. Appl. No. 11/825,212, dated Mar. 24, 2010.
Office Action for U.S. Appl. No. 11/825,212, dated Aug. 31, 2010.
Office Action for U.S. Appl. No. 11/825,212, dated Aug. 22, 2014.
International Search Report and Written Opinion for International Application No. PCT/US2007/089016, dated Jun. 17, 2008.
Office Action for U.S. Appl. No. 11/980,216, dated Dec. 24, 2008.
Office Action for U.S. Appl. No. 11/980,216, dated Jul. 20, 2009.
Office Action for U.S. Appl. No. 11/980,216, dated Jan. 5, 2010.
Office Action for U.S. Appl. No. 11/980,216, dated Jul. 2, 2010.
Office Action for U.S. Appl. No. 11/980,216, dated Jun. 19, 2014.
Office Action for U.S. Appl. No. 11/980,216, dated Feb. 17, 2015.
International Search Report and Written Opinion for International Application No. PCT/US2007/089017, dated Jun. 23, 2008.
Office Action for U.S. Appl. No. 11/985,162, dated Dec. 20, 2010.
Office Action for Canadian Application No. 2,848,274, dated Mar. 24, 2015, 3 pages.
European Search Report for European Application No. 13161632, dated Feb. 6, 2014.
Notice of Reasons for Rejection for Japanese Application No. 2013-246090, dated Dec. 2, 2014.
Notice of Grounds for Rejection for Korean Patent Application No. 2014-7008364, dated May 28, 2014.
Notice of Reasons for Rejection for Japanese Application No. 2015-111874, dated Apr. 18, 2016, 10 pages.
Office Action for U.S. Appl. No. 12/521,983, dated Feb. 15, 2012.
Office Action for U.S. Appl. No. 13/744,448, dated Jul. 15, 2013.
Office Action for U.S. Appl. No. 13/744,448, dated Apr. 9, 2014.
Office Action for U.S. Appl. No. 14/305,422, dated Apr. 27, 2016, 15 pages.
International Search Report and Written Opinion for International Application No. PCT/US2015/067404, dated Mar. 7, 2016, 10 pages.
Office Action for U.S. Appl. No. 15/589,607, dated Jul. 10, 2019, 12 pages.
Second Written Opinion for Singapore Application No. 11201704797T, dated Jan. 23, 2019, 7 pages.
Australian Examination Report for Australian Application No. 2015369710, dated Sep. 5, 2019, 4 pages.
Third Written Opinion for Singapore Application No. 11201704797T, dated Dec. 4, 2019, 7 pages.

\* cited by examiner

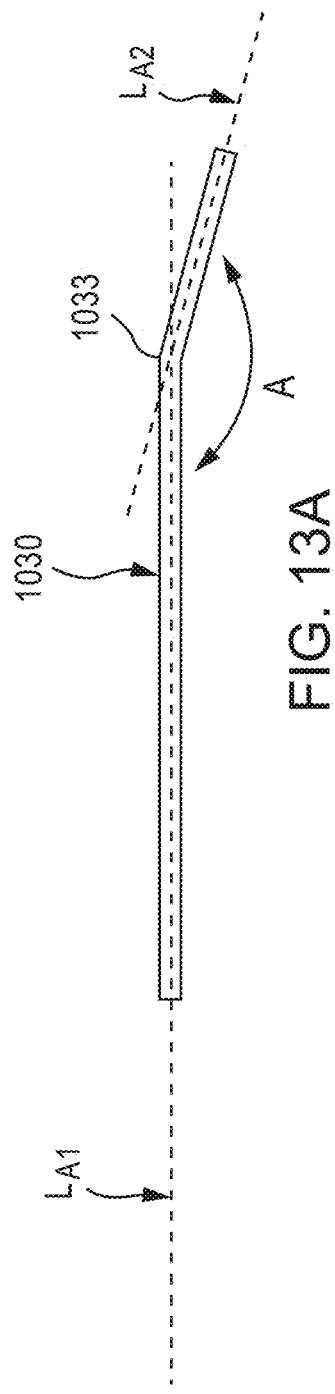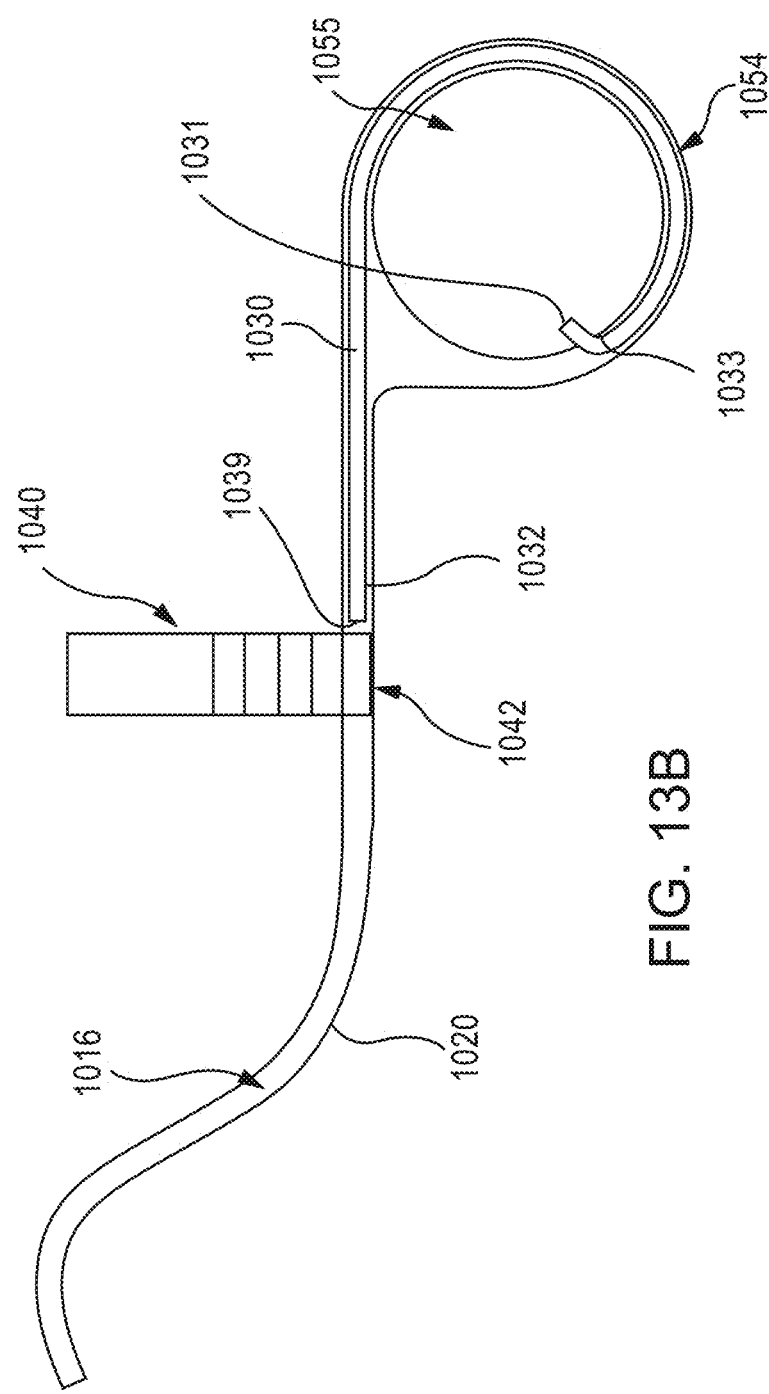

SYSTEMS, DEVICES AND METHODS FOR DISPENSING ORAL TRANSMUCOSAL DOSAGE FORMS

CROSS-REFERENCE TO RELATED APPLICATIONS

This application claims priority to and the benefit of U.S. provisional application Ser. No. 62/096,124, filed on Dec. 23, 2014, entitled "Devices and Methods for Dispensing Oral Transmucosal Dosage Forms," the disclosure of which is incorporated herein by reference in its entirety.

BACKGROUND

Devices, systems and methods described herein relate generally to drug dispensing devices and delivery mechanisms for administration of small-volume drug dosage forms.

Opioid drugs for Patient Controlled Analgesia (PCA) require special handling to ensure safe use by patients and to avoid misuse, diversion and abuse by patients, health care providers or other unauthorized subjects. Some known systems are configured to deliver small-volume drug dosage forms that release the opioid sufentanil for absorption through the oral mucosa. Such known delivery systems include a cartridge, which can hold many such small volume drug dosage forms; a dispenser that mates with the cartridge and enables proper placement of the dosage form adjacent the oral mucosa; and an electronic controller that enables dispensing of the dosage form from the cartridge in a prescribed manner. After the cartridge has been mated with the dispenser, inserted into the controller, and the system has been configured by a medical practitioner, it can be used to deliver a dosage form under the tongue of the patient.

To ensure patient safety in such known systems, it is important that the delivery system repeatably and reliably dispense one and only one dosage form during each dosage period. In an effort to mitigate the risk of misuse, diversion and/or abuse by patients, some known systems include a controller that imposes a locked-out state for a predetermined time period before another dosage form can be administered by the system. Other known systems include a cartridge that includes an initial "shipping" tablet that can be detected to notify the controller that a new cartridge has been loaded. In such systems, the controller can be initialized when the shipping tablet is detected. Moreover, some known systems track the delivery of each dosage form based on input received from a variety of sensors (e.g., optical sensors).

Some known devices, however, can be susceptible to improper and/or inaccurate delivery that can render safety control mechanisms less effective. In particular, some known drug dosage forms are formulated to be just a few millimeters in diameter and less than a millimeter in thickness. The small size of the dosage form can limit the precision with which delivery and/or detection of the delivery is performed. Moreover, sensor errors can result in an inadvertent lock-out or failure to maintain the device in a locked out state. Such sensor errors can be the result of calibration drift (over time as the system is repeatedly used), part-to-part variation (e.g., of the moving components in the delivery system) or the like. For example, some known systems determine the position of a delivery pushrod within a dispenser and detect the passage of a tablet through the track. Based upon data from the sensor, the controller software can calibrate the system, determine the position of the pushrod, and ascertain whether a single drug dosage form was released from the dispensing tip. If, however, the sensor reading deviates from an expected range of values, the software triggers a system error and the controller goes into a lock-out mode, which prevents further dosing until a health care professional intervenes.

It is also possible that the moving parts (e.g., a delivery pushrod) of a delivery system can operate in a discontinuous and/or inconsistent manner, causing a compromised delivery. Such inconsistent delivery can result from, for example, "binding" of a delivery member within the device (e.g., due to wear of the parts, manufacturing tolerances, impact of the environment and the like). As a result, dosage forms can be unevenly pushed through the delivery path, which can result in sensor errors, damage to the dosage form and/or improper delivery.

In some known dispensing devices, moving parts can change shape and properties due to fatigue, wear or plastic deformation from repeated use. Such part "drift" can reduce part-to-part clearance and cause the delivery member to bind, move erratically or seize within the passageway, thus causing an error state in the delivery device.

Thus, a need exists for improved methods and devices for delivering small-volume drug dosage forms. In particular, a need exists for a device and system that can be used for accurate and repeatable controlled delivery of a small dosage form (e.g., such as an opioid for treatment of pain), while reducing the potential for misuse, diversion or abuse by patients, health care providers or other unauthorized subjects, and which generates minimal, if any, lock-outs due to errors or malfunctions.

SUMMARY

In some embodiments, a drug delivery apparatus includes a pushrod configured to contact and move a dosage form through a passageway to deliver the dosage form. The pushrod is configured to consistently and repeatably move through the passageway within the dispenser without disruptions in its motion. In this manner, the instantaneous location of the pushrod and the solid drug dosage form within the pathway over multiple cycles is repeatable, and can be sensed with the desired accuracy. This arrangement reduces the number of detected or sensed fault conditions. Additionally, in some embodiments, the pushrod is configured such that its motion is repeatable over the lifetime of the dispensing device. Similarly stated, the pushrod is configured to remain substantially free of "kinks," non-uniform wear patterns and/or non-linearities over time, as any of these may prevent smooth motion of the pushrod in the passageway.

In some embodiments, an apparatus includes a housing and a pushrod. The housing defines a delivery passage and an exit port in fluid communication with the delivery passage. At least a portion of the pushrod is movably disposed in the delivery passage. A distal end portion of the pushrod is configured to move a drug dosage form through the delivery passage to convey the drug dosage form through the exit port when the distal end portion of the pushrod is moved from a first position to a second position. A surface of at least one of the pushrod or the housing defining the delivery passage is nonplanar, curved and/or contoured.

BRIEF DESCRIPTION OF THE DRAWINGS

FIGS. 13A and 13B are schematic illustrations of a pushrod, in a first configuration (free or undeformed state) and a second configuration (wrapped or deformed state), respectively, according to an embodiment.

DETAILED DESCRIPTION

Figure 1A:
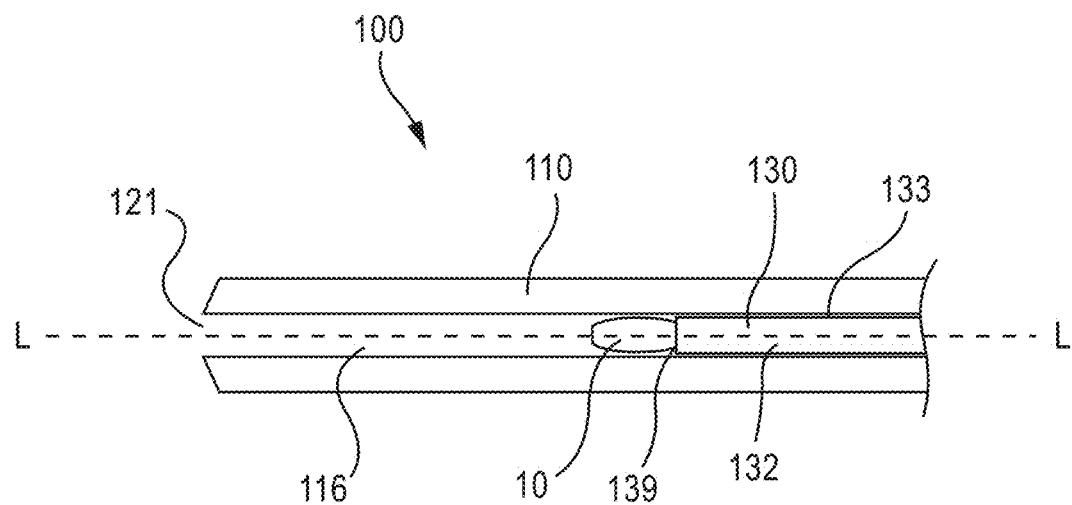
FIGS. 1A-1B are schematic illustrations of portions of a dosage delivery device according to an embodiment, in a first configuration and a second configuration, respectively.

Drug delivery devices for administration of solid dosage forms are described herein. In some embodiments, an apparatus includes a housing and a pushrod. The housing defines a delivery passage and an exit port in fluid communication with the delivery passage. At least a portion of the pushrod is movably disposed in the delivery passage. A distal end portion of the pushrod is configured to move a drug dosage form through the delivery passage to convey the drug dosage form through the exit port when the distal end portion of the pushrod is moved from a first position to a second position. A surface of at least one of the pushrod or the housing defining the delivery passage is nonplanar, curved and/or contoured.

In some embodiments, an apparatus includes a housing and a pushrod. The housing defines a delivery passage and an exit port in fluid communication with the delivery passage. At least a portion of the pushrod is movably disposed in the delivery passage. In particular, a distal end portion of the pushrod is configured to move a drug dosage form through the delivery passage to convey the drug dosage form through the exit port when the distal end portion of the pushrod is moved from a first position to a second position. A surface of the pushrod and/or a surface of the housing that defines the delivery passage is contoured such that the friction between the surface of the pushrod and the surface of the housing is reduced.

In some embodiments, an apparatus includes a housing and a pushrod. The housing defines a curved delivery passage and an exit port in fluid communication with the delivery passage. At least a portion of the pushrod is flexible and movably disposed in the delivery passage to convey a drug dosage form through the exit port when the distal end portion of the pushrod is moved from a first position to a second position. The housing and the pushrod are configured such that a distal end surface of the pushrod maintains contact with the drug dosage form when the pushrod is moved from the first position to the second position.

In some embodiments, an apparatus includes a housing and a pushrod. The housing defines a delivery passage and an exit port in fluid communication with the delivery passage. The housing also defines a hub volume within which a hub is rotatably disposed. A distal end portion of the pushrod is movably disposed in the delivery passage to convey a drug dosage form through the exit port when the distal end portion of the pushrod is moved from a first position to a second position. A proximal end portion of the pushrod is coupled to the hub such that rotation of the hub and the proximal end portion of the pushrod causes the distal end portion of the pushrod to move between the first position and the second position. At least one of a surface of the housing defining the hub volume or a surface of the proximal end portion of the pushrod is nonplanar.

In some embodiments, an apparatus includes a pushrod having a distal end portion configured to be movably disposed within a delivery passage of a drug delivery device to convey a drug dosage form through the delivery passage when the distal end portion of the pushrod is moved from a first position to a second position. A proximal end portion of the pushrod is configured to be coupled to a hub such that rotation of the hub and the proximal end portion of the pushrod causes the distal end portion of the pushrod to move between the first position and the second position. The proximal end portion of the pushrod forms an angle less than 180 degrees when in a relaxed configuration As used in this specification and the appended claims, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the words "a" or "an" and the phrase "one or more" may be used interchangeably.

As used herein, the words "proximal" and "distal" refer to the direction closer to and away from, respectively, an operator of the medical device. Thus, for example, the end of the dosage delivery device contacting, or otherwise nearest, the patient's body (e.g. within the mouth) would be the distal end of the dosage delivery device, while the end opposite the distal end would be the proximal end of the dosage delivery device.

As used herein, the terms "about" and/or "approximately" when used in conjunction with numerical values and/or ranges generally refer to those numerical values and/or ranges near to a recited numerical value and/or range. For example, in some instances, "about 40 [units]" can mean within ±25% of 40 (e.g., from 30 to 50). In some instances, the terms "about" and "approximately" can mean within ±10% of the recited value. In other instances, the terms "about" and "approximately" can mean within ±9%, ±8%, ±7%, ±6%, ±5%, ±4%, ±3%, ±2%, ±1%, less than ±1%, or any other value or range of values therein or therebelow. The terms "about" and "approximately" may be used interchangeably.

In a similar manner, term "substantially" when used in connection with, for example, a geometric relationship, a numerical value, and/or a range is intended to convey that the geometric relationship (or the structures described thereby), the number, and/or the range so defined is nominally the recited geometric relationship, number, and/or range. For example, two structures described herein as being "substantially parallel" is intended to convey that, although a parallel geometric relationship is desirable, some non-parallelism can occur in a "substantially parallel" arrangement. By way of another example, a structure defining a volume that is "substantially 0.50 milliliters (mL)" is intended to convey that, while the recited volume is desirable, some tolerances can occur when the volume is "substantially" the recited volume (e.g., 0.50 mL). Such tolerances can result from manufacturing tolerances, measurement tolerances, and/or other practical considerations (such as, for example, minute imperfections, age of a structure so defined, a pressure or a force exerted within a system, and/or the like). As described above, a suitable tolerance can be, for example, of ±1%, ±2%, ±3%, ±4%, ±5%, ±6%, ±7%, ±8%, ±9%, ±10%, or more of the stated geometric construction, numerical value, and/or range. Furthermore, although a numerical value modified by the term "substantially" can allow for and/or otherwise encompass a tolerance of the stated numerical value, it is not intended to exclude the exact numerical value stated.

While numerical ranges are provided for certain quantities, it is to be understood that these ranges can include all subranges therein. Thus, the range "from 50 to 80" includes all possible ranges therein (e.g., 51-79, 52-78, 53-77, 54-76, 55-75, 70-79, etc.). Furthermore, all values within a given range may be an endpoint for the range encompassed thereby (e.g., the range 50-80 includes the ranges with endpoints such as 55-80, 50-75, etc.).

The dosage delivery devices (also referred to herein as "delivery devices" or "dispensing devices" or "drug products") described herein can be used, for example, for administering a small volume drug dosage form to a subject. More specifically, the dosage delivery devices described herein can be used for oral (e.g. sublingual) administration of a bioadhesive small volume sufentanil-containing drug dosage form. Such dosage forms can be any of the dosage forms shown and described in U.S. Pat. No. 8,753,308, entitled "Methods for Administering Small Volume Oral Transmucosal Dosage Forms Using a Dispensing Device" ("the '308 patent"), the disclosure of which is incorporated herein by reference in its entirety. Moreover, the delivery devices shown herein can include any of the structure and/or features of any of the delivery devices shown in the '308 patent, such as, for example, a flexible pushrod, a cartridge configured to be removably coupled to the delivery device, optical detection of the location of the pushrod, a radiofrequency identification ("RFID") system or the like.

Figure 1B:
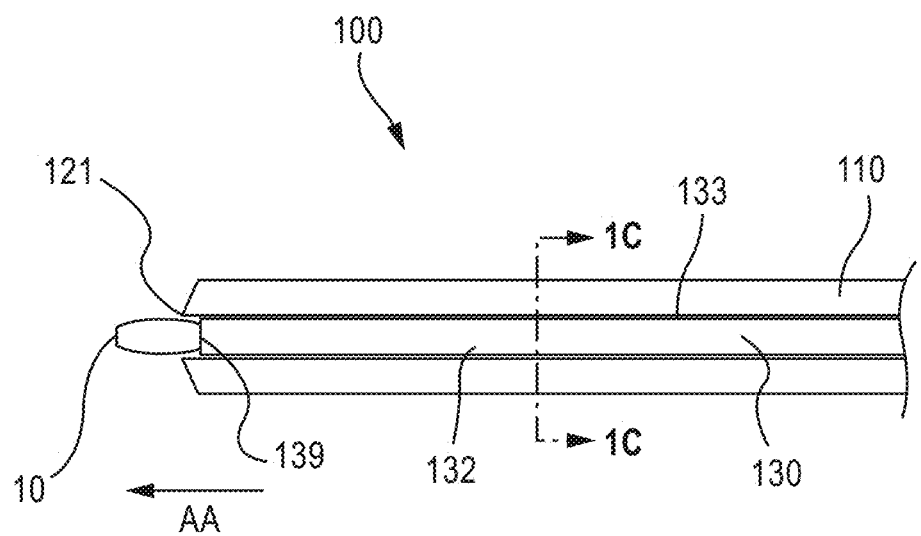
Figure 1C:
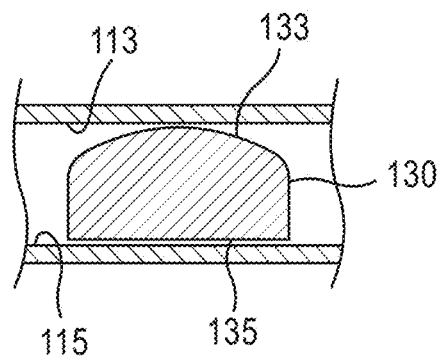
FIG. 1C is a cross-sectional view of a portion of the dosage delivery device shown in FIGS. 1A-1B taken along the line 1C-1C in FIG. 1B.

FIGS. 1A-1C are schematic illustrations of a portion of a dosage delivery device 100 according to an embodiment in a first configuration (FIG. 1A) and a second configuration (FIG. 1B), respectively. The dosage delivery device 100 is configured to deliver a dosage form 10 (also referred to herein as "drug dosage form") to a subject, as described herein, when the device is moved from its first configuration to its second configuration. The dosage delivery device 100 includes a housing 110 and a pushrod 130. The housing 110 defines a delivery passage 116 and an exit port 121 in fluid communication with the delivery passage 116. The pushrod 130 has a distal end portion 132 movably disposed in the delivery passage 116. Upon actuation of the dosage delivery device 100, the pushrod 130 is moved within the delivery passage 116 such that the distal end portion 132 of the pushrod contacts the dosage form 10 disposed within the delivery passage. The dosage form 10 can be moved into the delivery passage in any suitable manner. For example, the dosage form 10 can be conveyed from a cartridge coupled to the device 100 into the delivery passage 116, as described in more detail herein, such as with respect to FIGS. 4 and 11. The distal end portion 132 of the pushrod 130 is configured to move the dosage form 10 through the delivery passage 116 when the pushrod is moved in a first direction within the delivery passage, also upon actuation of the dosage delivery device 100, as shown by the arrow AA in FIG. 1B. Said another way, the distal end portion 132 of the pushrod 130 is configured to move in the first direction from a first position with respect to the delivery passage (see, e.g., FIG. 1A) to a second position with respect to the delivery passage. In this manner, movement of the pushrod 130 in the first direction can convey the dosage form 10 through the exit port 121 such that the dosage form 10 is expelled or delivered from the delivery passage 116. In some embodiments, the distal end portion 132 of the pushrod 130 is disposed within the delivery passage 116 when the pushrod is in its first position. In some embodiments, the distal end portion 132 of the pushrod 130 is disposed within the delivery passage 116 when the pushrod is in its second position, as shown in FIG. 1B. In some embodiments, the distal end portion 132 of the pushrod 130 is at least partially extended from the delivery passage 116, through the exit port 121, when the pushrod is in its second position (not shown).

The exit port 121 of the housing 110 can be at least partially surrounded by a shroud (not shown), seal (not shown) or other structure to guide delivery of the drug dosage form 10 when the dosage form 10 is expelled or otherwise delivered from the delivery passage 116 through the exit port and/or to limit the ingress of moisture into the delivery passage 116. Suitable shrouds, seals, and other mechanisms to guide delivery of the dosage form 10 and/or limit the ingress of moisture into the delivery passage are shown and described in the '308 patent.

At least a portion of the pushrod 130 is configured to contact, or engage, at least a portion of the housing 110 defining the delivery passage 116 (e.g., a wall of the delivery passage) when the pushrod is moved within the delivery passage, such as from its first position to its second position. It should be noted that the pushrod 130 is shown in FIGS. 1A-1C as being spaced apart from the housing 110 for purposes of clarity of illustration. In some embodiments, at least a portion of the pushrod 130 is configured to slidingly contact the portion of the housing defining the delivery passage 116 when the pushrod is moved therein. For example, the pushrod can include a first or "upper" surface 133, at least a portion of which slidingly contacts a first surface 113, or surface portion, of the housing 110 defining the delivery passage 116, a second or "lower" surface 135, at least a portion of which slidingly contacts a second surface 115, or surface portion, of the housing 110 defining the delivery passage 116, or both such first and second surfaces. In some embodiments, the push rod 130 can include one or more side surfaces extended between the first and second surfaces 133, 135. At least a portion of one or more of the side surfaces can slidingly contact one or more surfaces of the housing 110 defining the delivery passage 116, such as a portion of one or more surfaces extending between the first surface 113 of the housing and the second surface 115 of the housing, when the pushrod 130 is moved therein.

Movement of the pushrod 130 is controlled by a drive system (not shown in these figures) of the dosage delivery device 100. The drive system can include, for example, a motor configured to produce a driving force that causes the pushrod to move within the delivery passage 116. The drive system is configured, upon actuation of an actuator of the device 100, to move the pushrod 130 through the delivery passage 116, for example, at a speed sufficient to produce a force sufficient to move the dosage form 10 through the delivery passage 116 towards and through the exit port 121 of the dosage delivery device 100. The speed at which the pushrod 130 engages or otherwise contacts the dosage form 10 produces a force on the dosage form 10 sufficient to ensure the distal end surface 139 of the pushrod 130 maintains contact with the dosage form 10 as the dosage form 10 is moved through the delivery passage 116.

Such constant contact between the distal end surface 139 of the pushrod 130 and the dosage form 10 after the pushrod 130 initially contacts the dosage form within the delivery passage 116 helps to ensure that the dosage form is moved through the delivery passage 116 and delivered or expelled from the exit port 121 of the device 100 in a desirable manner. Said another way, the contact between the distal end surface 139 of the pushrod 130 and the dosage form 10 prevents the dosage form from being "flicked" or otherwise moved away from the distal end surface 139 of the pushrod 130 upon initial contact therebetween or as the pushrod 130 moves the dosage form 10 through the delivery passage 116 after such initial contact therebetween.

In turn, the drive force produced by the drive system is intended to provide for a predictable trajectory of movement of the dosage form 10 upon being expelled from the dosage delivery device 100, thus helping to ensure the dosage form is directed to a desired location of the subject's anatomy. Additionally, this helps to ensure the dosage form 10 remains intact during delivery from the dosage delivery device 100, as improper contact between the dosage form 10 and the pushrod 130 may cause the dosage form to crack, break, or shatter during a delivery event, which could impair proper delivery of the dosage form 10 from the device 100 and/or proper placement of the dosage form 10 with respect to the subject's anatomy. For example, a cracked, broken, or shattered dosage form may not follow the same trajectory of motion as an intact dosage form upon being expelled from the exit port 121, and thus may not be delivered to a target location of the subject.

The force applied to the pushrod 130 by the drive system is configured to overcome frictional force resisting movement of the pushrod 130 through the delivery passage 116, like those that may result from the sliding contact between one or more surfaces of the pushrod 130 and one or more surfaces of the portion of the housing 110 defining the delivery passage 116. The pushrod 130 and the housing 110 are collectively configured to reduce the occurrence of and/or magnitude of frictional contact therebetween such that the driving force will produce a predetermined rate of movement of the distal end surface 139 of the pushrod 130. In some embodiments, for example, the pushrod 130 and the housing 110 are collectively configured to reduce the occurrence of and/or magnitude of frictional contact therebetween such that the driving force will produce a non-negative acceleration of the distal end surface 139 of the pushrod 130 for at least a portion, but not necessarily an entirety, of the length of the delivery passage 116. In other words, the dosage delivery device 100 can be configured such that the distal end surface 139 of the pushrod 130 is moved within the delivery passage 116 such that the speed of movement of the distal end surface does not decrease and subsequently increase as the pushrod 130 moves the dosage form 10 through the portion of the delivery passage 116. In some embodiments, the pushrod 130 and the housing 110 are collectively configured to reduce the occurrence of and/or magnitude of frictional contact therebetween such that the driving force will produce a constant velocity of movement of the distal end surface 139 of the pushrod 130 for at least a portion, but not necessarily an entirety, of the length of the delivery passage.

Said another way, in some embodiments, the pushrod 130 and the housing 110 are collectively configured such that, in the presence of such sliding contact between one or more surfaces (e.g., first surface 133) of the pushrod and one or more surfaces (e.g., surface 113) of the housing defining the delivery passage upon actuation of the dosage delivery device 100, a substantially consistent and/or uniform movement of the pushrod 130 within the delivery passage 116 is produced. More specifically, in some embodiments, the pushrod 130 and the housing 110 are collectively configured such that contact of the one or more surfaces of the pushrod and one or more surfaces of the housing during movement of the pushrod within the delivery passage facilitates the substantially consistent and/or uniform movement of the pushrod therein. In this manner, the pushrod 130 and the housing 110 can be collectively configured such that, upon actuation of the dosage delivery device 100, the distal end portion 132 of the pushrod 130 moves within at least a portion of the delivery passage 116 with a substantially constant velocity or acceleration.

In some embodiments, at least one surface of the pushrod 130 is configured to facilitate such movement of the pushrod within the delivery passage 116. For example, at least one surface of the pushrod 130 can be configured such that less than an entirety of the area of at least one surface of the pushrod 130 (or portion thereof) is in sliding contact with the portion of the housing 110 defining the delivery passage 116, such as the first surface 133 of the housing, for at least one location of the delivery passage. In some embodiments, as shown in FIG. 1C, the first surface 133 of the pushrod 130 is nonplanar, or at least includes a nonplanar portion. More particularly, the surface 133 of the pushrod 130 can be nonplanar when taken along a cross-section normal to a longitudinal axis L of the pushrod 130, as shown in FIG. 1A. Even more specifically, the first surface 133 of the pushrod 130 can be curved, or convex, as shown in FIG. 1C. In other embodiments, however, the first surface 133 of the pushrod 130 can have a different nonplanar shape, as described herein. As also shown in FIG. 1C, the second surface 135 of the pushrod 130, opposite the first surface, is planar (or has a greater planar surface area than the first surface 133 of the pushrod 130), although in other embodiments, the second surface can have a different (e.g., nonplanar) shape, contour or profile.

The nonplanar surface 133 of the pushrod 130 is shown in FIG. 1C as being the "upper" surface, but in other embodiments, any surface, or combination of surfaces, of the pushrod 130 that is in sliding contact with the portion of the housing 110 that defines the delivery passage 116 can be nonplanar, contoured or otherwise shaped. This arrangement reduces or minimizes the surface area of the first surface 133, and thus the surface area of the pushrod 130 as a whole, that is in contact with the housing 110 during movement of the pushrod 130 within the delivery passage 116. In this manner, the amount of contact area, and thus friction, between the pushrod 130 and the housing 110 during delivery of the dosage form 10 can be reduced (as compared to the contact, or friction, that would otherwise result from movement within the delivery passage of a pushrod with a greater surface area contacting the housing, which may occur for a pushrod having a square or rectangular cross-section, or planar surface).

The reduced contact surface area collectively between the pushrod 130 and the portion of the housing 110 defining the delivery passage 116 helps to produce the substantially consistent, repeatable movement of the pushrod 130 within the delivery passage 116. Said another way, the reduced contact surface area collectively between the pushrod 130 and the portion of the housing 110 defining the delivery passage 116 is configured to prevent the occurrence of and/or reduce the magnitude of an occurrence of frictional contact therebetween, thereby also preventing an unintentional deceleration of at least a portion the pushrod (e.g., as may be caused by the pushrod "catching" on a surface of the housing) and subsequent acceleration of the portion of the pushrod at a rate greater than that the rate of acceleration provided by the driving force of the drive system in the absence of such frictional contact (e.g., as may occur as a result of the pent up force when the drive force overcomes the pushrod being "caught" on the surface of the housing and the pushrod is released or the frictional contact is overcome).

In turn, this provides for a consistent, repeatable engagement or contact of the pushrod 130 with the dosage form 10 within the delivery passage 116 upon actuation of the device 100 and/or a substantially consistent, repeatable speed of movement or acceleration of the distal end portion 132 of the pushrod 130 within (and thus also a substantially consistent, repeatable speed of movement or acceleration of the dosage form 10 through) the delivery passage and delivery of the dosage form 10 through the exit port 121 of the dosage delivery device 100. More specifically, the reduced contact surface area collectively defined by the pushrod 130 and the portion of the housing 110 defining the delivery passage 116 facilitates, in some embodiments, a consistent speed or velocity of movement and/or a consistent acceleration of the distal end portion 132 of the pushrod 130 through the delivery passage 116 during a single actuation. Said another way, in some embodiments, the distal end portion 132 of the pushrod 130 moves through a first location of the delivery passage 116 at a first rate of speed and through a second location of the delivery passage, distal to the first location, at the first rate of speed during a single actuation of the dosage delivery device 100. In some embodiments, the distal end portion 132 of the pushrod 130 moves at a first acceleration through a first location of the delivery passage 116 and at the first acceleration through a second location of the delivery passage, distal to the first location, during a single actuation of the dosage delivery device 100.

Also in this manner, the housing 110 and the pushrod 130 are collectively configured such that a distal end surface 139 of the pushrod maintains contact with the drug dosage form 10 when the pushrod is moved from the first position to the second position. Further, the reduced contact surface area collectively defined by the pushrod 130 and the portion of the housing 110 defining the delivery passage 116 facilitates a consistent speed or velocity of movement or a consistent, non-negative rate of acceleration of the distal end portion 132 of the pushrod 130 through the delivery passage 116 during actuation of the dosage delivery device 100 at a first period of time and during actuation of the dosage delivery device at a second period of time after the first period of time.

Although the dosage delivery device 100 is shown and described as including a pushrod 130 having a surface configured to facilitate the substantially consistent and/or uniform movement of the pushrod within the delivery passage 116 of the housing 110, in some embodiments, at least one surface of a housing of a dosage delivery device defines a delivery passage configured to facilitate such consistent and/or uniform movement of the pushrod within the delivery passage. For example, at least one surface of the housing defining the delivery passage 116 can be configured such that less than an entirety of the surface (or surface portion) of the housing 110 defining the delivery passage is in sliding contact with the pushrod 130. For example, although FIGS. 1A-1C show the pushrod 130 as having a nonplanar and/or contoured surface 133, in other embodiments, the portion the housing 110 that defines the delivery passage 116 can include a nonplanar and/or contoured surface. In such embodiments, the pushrod can have (but does not necessarily have) one or more planar and/or flat contact surfaces, as described herein.

Figure 1D:
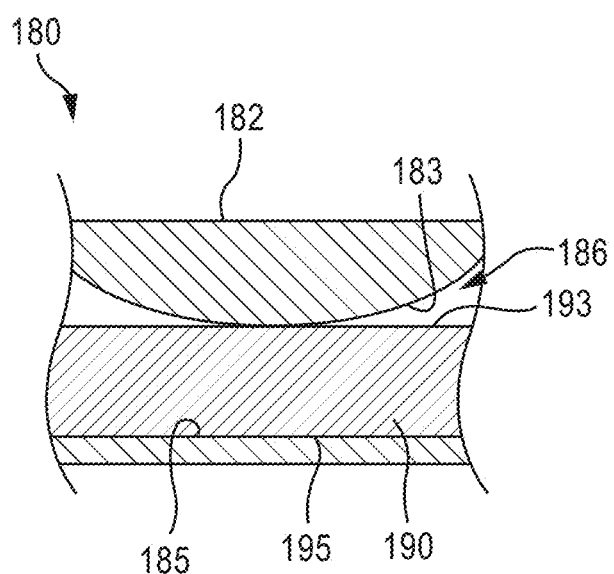
FIG. 1D is a cross-sectional view of a portion of a dosage delivery device according to an embodiment.

For example, referring to FIG. 1D, in some embodiments, a drug delivery device 180 includes a housing 182 defining a delivery passage 186 and a pushrod 190 movably disposed within the delivery passage 186. A portion of the housing 182 defining the delivery passage 186 can include a first surface 183 that is nonplanar (e.g., convex or curved, as shown in FIG. 1D) and a second surface 185 that is planar. The pushrod 190 is substantially planar on its first, or upper, surface 193 and its second, or lower, surface 195. In other embodiments, however, the second surface 185 of the housing 182 can be nonplanar and/or contoured instead of, or in addition to, the first surface 183 being nonplanar and/or contoured. Other suitable surface geometries, contours, and/or textures for one or more surfaces of the portion of the housing defining the delivery passage are described herein.

In some embodiments, a pushrod can include a surface contour and/or profile that varies spatially along a longitudinal axis of the pushrod. This arrangement can be used, for example, in a delivery device in which the delivery passage is curved, or includes one or more curved portions. In such embodiments, at least a first portion of the pushrod that will traverse a bend or curve of the delivery passage can have a first contact area, whereas at least a second portion of the pushrod can have a second, different, contact area.

Figure 2:
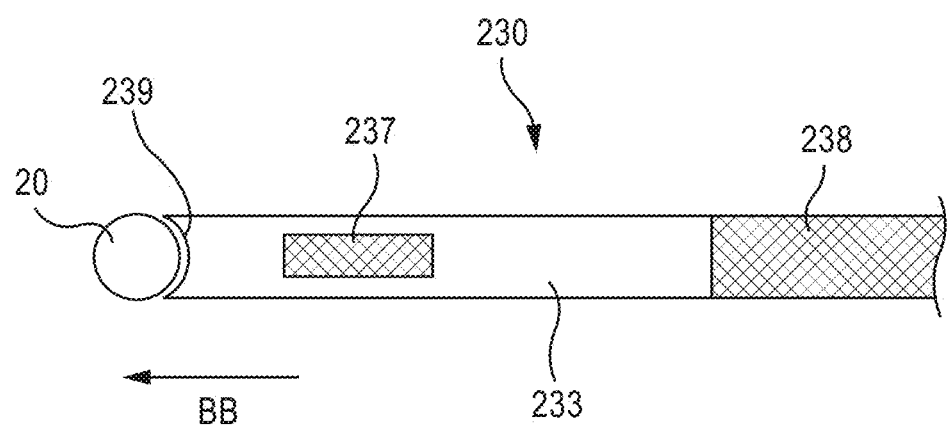
FIG. 2 is a top view of a portion of a pushrod of a dosage delivery device according to an embodiment.

For example, FIG. 2 shows a top view of a pushrod 230 that can be used in any of the devices or embodiments shown and/or described herein, or in the '308 patent. The pushrod 230 includes a distal end surface 239 that contacts a drug dosage form 20. The distal end surface 239 can be contoured and/or shaped to receive and/or matingly engage the drug dosage form 20. For example, as shown in FIG. 2, the distal end surface 239 of the pushrod 230 can define a semi-circle shaped recess, or otherwise concave end, configured to matingly engage a curved outer surface of the dosage form 20 when the pushrod 230 is moved in a first direction, as shown by arrow BB, from a first position to a second position. For example, in some embodiments, the distal end surface 239 is configured to engage the dosage form when the pushrod 230 is at a third position between the first position and the second position.

A top surface 233 of the pushrod 230 includes a first contact surface 237 and a second contact surface 238. The first contact surface 237 can be nonplanar, contoured or otherwise include protrusions or any suitable surface geometry described herein, as represented by the hatched pattern. The second contact surface 238 can be nonplanar, contoured or otherwise include protrusions or any suitable surface geometry described herein, as represented by the hatched pattern. The physical characteristics (e.g., size, length, width, shape, type of contour, depth of contour, height of protrusion, or the like) of the first contact surface 237 can be different from the physical characteristics of the second contact surface 238. Similarly stated, the characteristics of the top surface 233 of the pushrod can vary at different locations of the pushrod spaced apart along the longitudinal axis thereof. Although the first contact surface 237 and second contact surface 238 are shown and described as being included on the top surface 233 of the pushrod 230, in some embodiments, the first contact surface can be on a first surface or side of the pushrod (e.g., the top surface) and the second contact surface can be on a second surface or side of the pushrod different from the first surface (e.g., a bottom surface).

Figure 3:
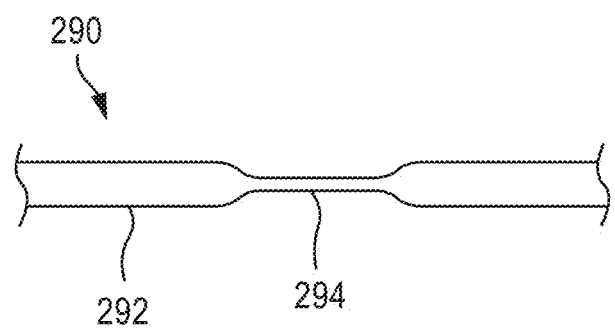
FIG. 3 is a top view of a portion of a pushrod of a dosage delivery device according to an embodiment.

Although the overall width of the pushrod 230 is shown as being substantially constant along a length of the pushrod coaxial with its longitudinal axis, in other embodiments, the width can vary along the longitudinal axis. Said another way, a pushrod of a dosage delivery device according to an embodiment (see, e.g., FIG. 3) can include a pushrod 290 having a first width at a first location 292 of the pushrod and a second width at a second location 294 of the pushrod different from (e.g., less than or narrower than) the width at the first location. Further, the first location can be proximal to or distal to the second location. Said another way, the first location 292 of the pushrod 290 can be a first distance from a distal end surface (not shown in FIG. 3) of the pushrod, and the second location 294 of the pushrod 290 can be a second distance from the distal end surface of the pushrod different (e.g., lesser than or greater than) the first distance. In this manner, the cross-section moment of inertia (e.g., the moment of inertia as calculated for a rectangular cross-sectional area) can be varied along the longitudinal axis of the pushrod 290. In this manner, the pushrod 290 can be configured to have certain portions (e.g., a narrower portion of the pushrod) that are more flexible than other portions (e.g., a wider portion of the pushrod).

Figure 4:
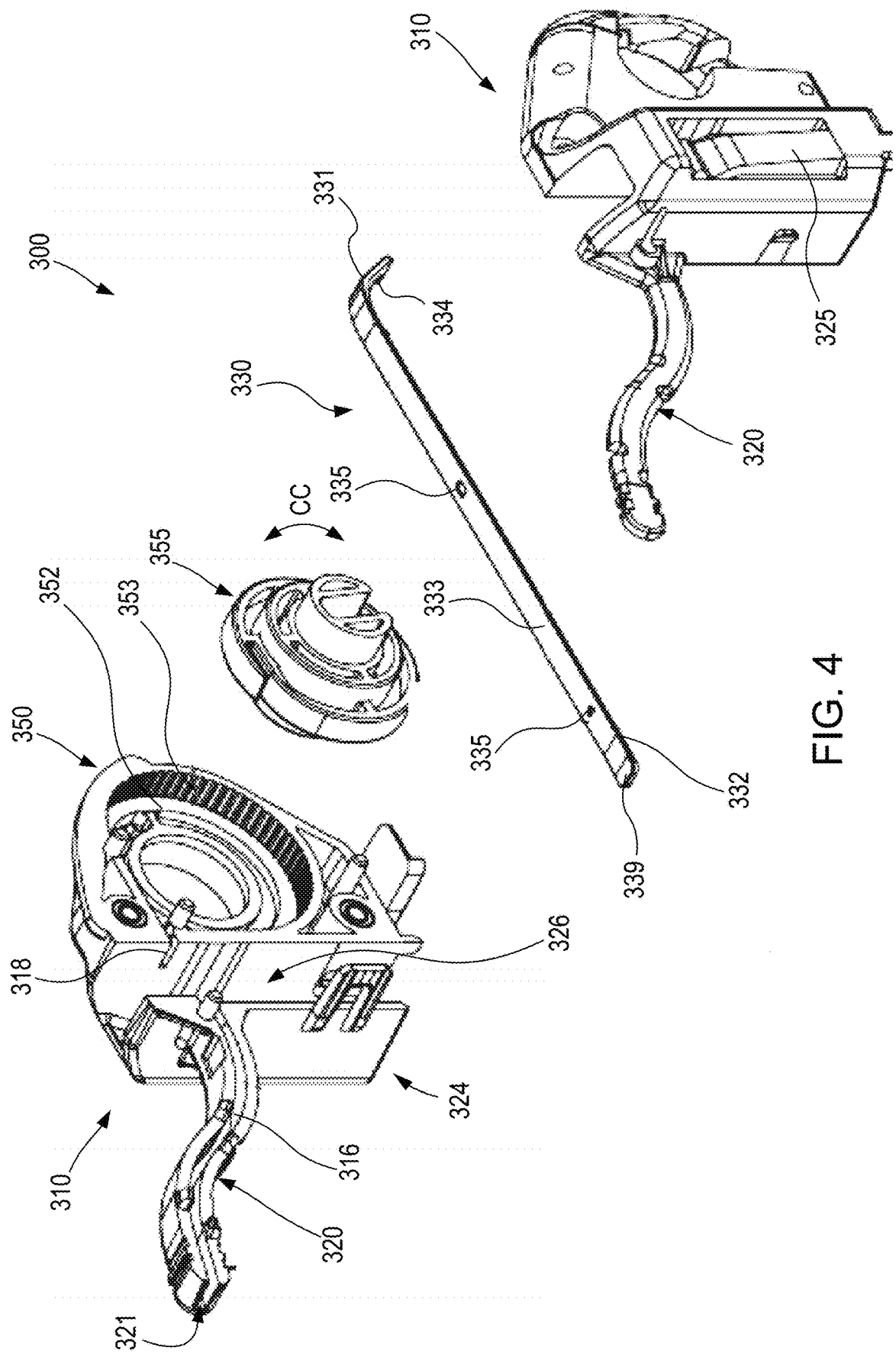
FIG. 4 is an exploded perspective view of a portion of a dosage delivery device according to an embodiment.

FIG. 4 is an exploded view of a portion of a dispensing device 300 according to an embodiment. The dispensing (or delivery) device 300 includes a housing 310, an actuator hub 355 and a pushrod 330. The housing 310 includes a proboscis portion 320, a cartridge receiving portion 324, and an actuator (or hub) portion 350. The proboscis portion 320 defines at least a portion of a delivery passage 316 and an exit port 321 at a distal end of the delivery passage 316. The delivery passage 316 has a length greater than its width, and is curvilinear. More specifically, the delivery passage 316 includes at least one bend or curve along the length of the delivery passage. The delivery passage 316 is configured to receive at least a portion of the pushrod 330, as described herein.

The cartridge receiving portion 324 defines a cartridge volume 326 within which a cartridge (not shown) can be removably coupled to the dispensing device 300. Any suitable cartridge can be coupled to the dispensing device 300 via the cartridge receiving portion 324 and the cartridge can contain a series of drug dosage forms (and/or a "shipping tablet), as described in the '308 patent. The cartridge can include a key or other locking feature configured to mate with at least one locking tab 325 of the housing 310. For example, the locking tab 325 can be inwardly biased towards the cartridge volume 326 defined by the cartridge receiving portion such that the locking tab 325 engages or mates with a portion of a cartridge received in the cartridge volume 326.

The actuator (or hub) portion 350 defines a hub volume 352 within which the hub 355 is rotatably mounted. The actuator portion 350 includes an inner surface 353 that defines the hub volume 352. In some embodiments, a portion of the pushrod 330 (i.e., a first surface 333) contacts at least a portion of the inner surface 353 of the actuator portion 350 when the dispensing device 300 is actuated. The hub portion 350 also defines a pushrod pathway 318, which is a pathway or opening within which a distal end portion 332 of the pushrod 330 can move within the hub portion 350 during dispensation of a dosage form. In some embodiments, the pushrod pathway 318 is at least partially disposed about the hub volume 352.

The pushrod pathway 318 can be in fluid communication with at least one of the delivery passage 316 of the proboscis or an opening in the cartridge containing the dosage forms. In particular, upon actuation of the device 300, the distal end portion 332 of the pushrod 330 is moved in a first direction within the pushrod pathway 318 and into the cartridge volume 326. In the cartridge volume 326, the distal end portion 332 can engage a dosage form from the cartridge received in the cartridge receiving portion 324. In some embodiments, upon actuation of the device 300, the distal end portion 332 of the pushrod 330 is moved within the pushrod pathway 318, into the cartridge volume 326 and through an opening defined by the cartridge where the distal end portion 332 of the pushrod 330 engages or contacts the dosage form. The distal end portion 332 of the pushrod 330 then continues to move in the first direction into and within the delivery passage 316 of the proboscis portion 320 to convey the dosage form through the proboscis portion 320 of the housing and through the exit port 321. Although the distal end portion 332 of the pushrod 330 is described herein as being moved through an opening of the cartridge coupled to the device 300 upon actuation of the device to engage a dosage form, in some embodiments, the distal end portion 332 of the pushrod 330 moves adjacent to or over an opening of the cartridge to engage a dosage form.

The pushrod 330 includes a proximal end portion 331 and the distal end portion 332. At least a portion of the pushrod 330, such as a portion between the proximal end portion 331 and the distal end portion 332, is flexible. In this manner, the pushrod 330 is configured to move through one or more nonlinear passages defined by the device 300, such as the delivery passage 316. As described herein, the proximal end portion 331 of the pushrod 330 is coupled to the hub 355. As also described herein, the distal end portion 332 of the pushrod 330 is configured to move within the delivery passage 316 to dispense a drug dosage form from the device 300. In some embodiments, the pushrod 330 defines one or more openings 335, or windows, therethrough that interact with an optical detection system (not shown) of the device 300. Said another way, in some embodiments, the pushrod 330 defines at least a first portion 335 that is transparent to the optical detection system, such as to a sensor of the optical detection system, and at least a second portion that is opaque to the optical detection system (or sensor thereof). Suitable optical detection systems are described in the '308 patent. In this manner, the position of the pushrod 330 within the delivery passage 316 can be detected. Also in this manner, the device 300 can be calibrated based on the detection of the position of the pushrod 330 and/or other input received from the optical detection system.

The pushrod 330 includes the first surface 333 and a second surface 334, opposite the first surface. The first surface 333 can be, for example, a top surface of the pushrod 330 when the pushrod is in an undeformed configuration, described in more detail herein, or an outer surface of the pushrod at least a portion of which faces away from the hub (e.g., towards the inner surface 353 of the actuator portion 350) when the pushrod is in a deformed configuration and coupled to the hub 355, as described in more detail herein. The second surface of the pushrod 330 can be, for example, a bottom surface of the pushrod when the pushrod is in the undeformed configuration, or an inner surface of the pushrod at least a portion of which faces the hub 355 when the pushrod is in a deformed configuration and coupled to the hub 355. The first surface 333, the second surface 334, or each of the first and second surfaces, or one or more portions thereof, can be contoured, nonplanar, or have any surface geometry according to any embodiment described herein. For example, in some embodiments, the pushrod 330 can have a first contact surface and a second contact surface, each disposed on a surface or side of the pushrod, as described herein with respect to pushrod 230 and FIG. 2.

The hub 355 is configured to rotate with respect to the actuator portion 350 in a first direction and a second direction opposite the first direction, as shown by arrow CC in FIG. 4. In some embodiments, the hub 355 is actuated by a motor. Upon actuation, the hub rotates in the first direction to drive at least a portion of the pushrod 330 through the pushrod pathway 318 and towards or through the delivery passage 316. After dispensing the dosage form, the hub 355 rotates in the second direction to retract the pushrod 330 from the delivery passage 316 and/or the pushrod pathway 318.

Due to the curvature of the hub volume 352 and portions of the pushrod pathway 318, at least one portion of the pushrod 330 can contact at least a portion of the inner surface 353 of the housing 310 when the pushrod is driven by the hub 355, either in the first direction or in the second direction. In particular, the proximal end portion 331 of the pushrod is coupled to the hub 355, and at least a portion of the first surface 333 of the pushrod contacts at least a portion of the inner surface 353 of the actuator portion 350 when the pushrod is moved by the hub 355. For example, at least a portion of the distal end portion 332 of the pushrod 330 can contact at least a portion of the inner surface 353, when the pushrod is wound around the hub prior to actuation of the device 300. In another example, at least a portion of the proximal end portion 331 of the pushrod can contact at least a portion of the inner surface 353 of the actuator portion 350 when the hub 355 moves the pushrod upon actuation of the device 300. In still another example, at least a portion of the pushrod 330 between its proximal end portion 331 and its distal end portion 332 can contact at least a portion of the inner surface 353 of the actuator portion 350 during at least one time period as the hub 355 drives the pushrod 330, in either the first direction or second direction.

In use, the pushrod 330 may contact one or more surfaces (walls) of the delivery passage 316, the pushrod pathway 318 and/or the inner surface 353 of the actuator portion 350 during movement of the pushrod therethrough (e.g., as the distal end portion 332 of the pushrod is moved or advanced towards the exit port 321 or is moved or retracted towards the hub 355. As discussed above, with respect to dosage delivery device 100, if force(s) exerted on the pushrod 330 because of such contact are non-uniform, the motion of the pushrod may become non-linear and/or discontinuous. Similarly stated, if contact forces exerted on the pushrod 330 vary greatly from one cycle (or actuation) to the next, the pushrod motion could potentially vary from one cycle (or actuation) to the next. Additionally, variance in the frictional forces resulting from such contact can result in uneven or "jerky" pushrod motion during a single delivery event (or actuation). In such situations, one or more sensors, such as the sensor of the optical detection system, configured to sense the pushrod 330 location (e.g., via the one or more openings 335 or transparent portions) may detect a location or position of the pushrod indicative of a malfunction in the pushrod actuation mechanism or in the delivery of the drug dosage form. For example, in such situations, at least one opening 335 of the pushrod 330 may not be detected by the sensor at a predetermined time after actuation of the device was initiated, thus indicating that the pushrod experienced a change in speed or velocity during the delivery event. Moreover, under such circumstances, the drug dosage form can become separated or spaced apart from a distal end surface 339 of the distal end portion 332 of the pushrod 330, which can result in improper delivery of the dosage form from the device 300. In some embodiments, in response to the sensor detecting a location or position of the pushrod indicative of a malfunction, the dispensing device 300 is configured to be placed into, or automatically enter, a locked-out state. Suitable lockout mechanisms are described in detail in the '308 patent.

Accordingly, in some embodiments, at least one surface of the housing 310 (e.g., a surface of the proboscis portion 320 defining the delivery passage 316, a surface of the actuator portion 350 defining the pushrod pathway 318, a portion of the inner surface 353 of the actuator portion 350 disposed about the hub 355) and/or the pushrod 330 (e.g., the first surface 333 or the second surface 334) can be contoured, nonplanar and/or can include other physical features or characteristics to reduce frictional resistance to movement of the pushrod (e.g., during a delivery event). Said another way, at least one surface of the housing 310 and/or the pushrod 330 can be configured with a reduced surface area at a portion of the housing 310 and/or the pushrod 330 that can contact the other of the pushrod or the housing during movement of the pushrod therein. The physical features or characteristics of such a surface of the housing 310 and/or the pushrod 330 can be referred to as a contact reducing surface profile. As used herein, and unless the context clearly dictates otherwise, reference to "at least one surface" can include a portion of the surface or the entirety of the surface, and can also include one, two, three or more discrete or non-contiguous portions of the surface that can each vary spatially across a length, width, or diagonal of the surface.

Any suitable contact reducing surface profile can be included in on at least one surface of the housing 310 (e.g., a surface of the proboscis portion 320 defining the delivery passage 316, a surface of the actuator portion 350 defining the pushrod pathway 318, a portion of the inner surface 353 of the actuator portion 350 disposed about the hub 355) and/or the pushrod 330 (e.g., the first surface 333 or the second surface). For example, in some embodiments, the at least one surface of the housing 310 and/or the pushrod 330 can include a contact reducing surface profile including one or more teeth, protrusions, curves or the like. In this manner, the area of contact between the housing 310 and the pushrod 330 can be reduced.

Figure 5A:
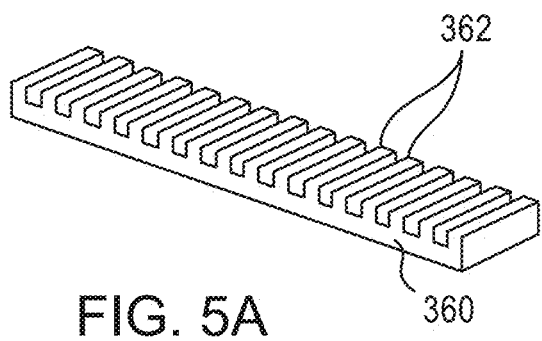
FIG. 5A is a perspective view of a surface geometry of a portion of a dosage delivery device according to an embodiment.
Figure 5B:
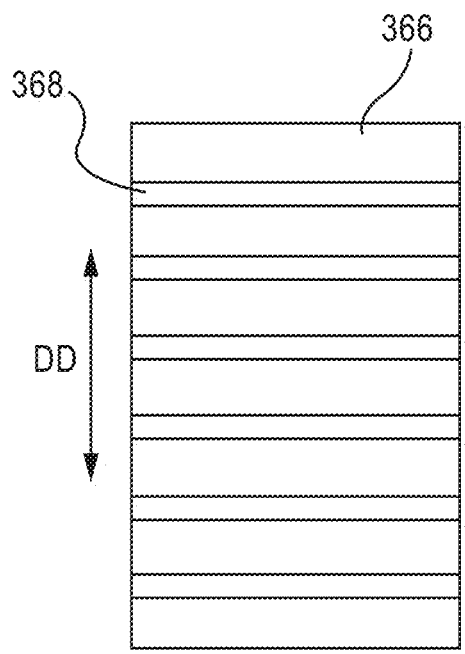
FIGS. 5B-5D are top views of surface geometries of a portion of a dosage delivery device according to an embodiments.

For example, in some embodiments, referring to FIGS. 5A and 5B, a surface 360, 366 has a contact reducing surface profile that includes raised parallel teeth 362, 368, respectively. The teeth 362, 368 are arranged spaced apart along a length of the surface 360, 366, respectively, with each tooth having an elongate axis that extends substantially perpendicular to a direction of motion of the pushrod, represented by arrow DD in FIG. 5B. The inner surface 353 of delivery device 300 is shown in FIG. 4 as including such raised parallel teeth.

Figure 5C:
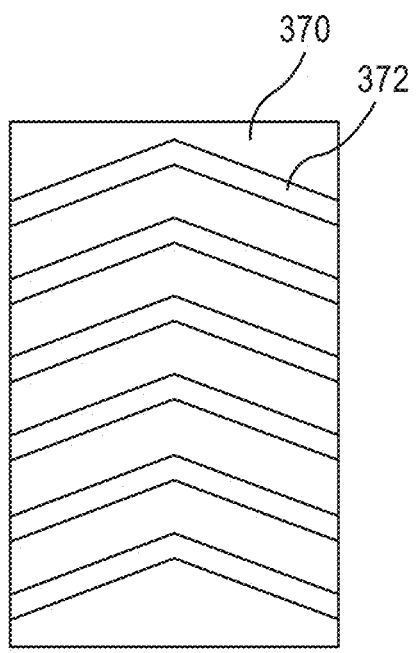
Figure 5D:
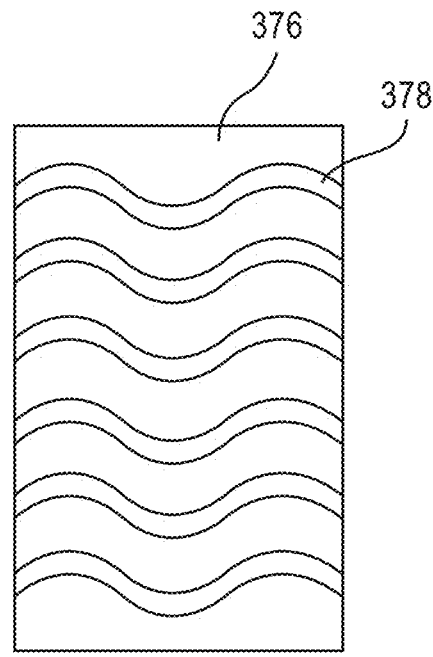

In some embodiments, referring to FIG. 5C, a surface 370 includes parallel v-shaped teeth 372 or parallel teeth 372 arranged in a herringbone pattern or chevron pattern, in which the vertex of each tooth 372 is aligned with the axis of motion of the pushrod. In some embodiments, referring to FIG. 5D, a surface 376 includes teeth 378 that are arranged along parallel sinusoidal curves with each tooth 378 having an axis that is substantially perpendicular to the direction of motion of the pushrod. In a delivery device according to an embodiment described herein, in which a surface of the housing includes the plurality of teeth, at least one tooth is configured to contact a pushrod of the delivery device. In a similar manner, in a delivery device according to an embodiment described herein, in which a surface of the pushrod includes the plurality of teeth, at least one tooth is configured to contact a surface of the housing of the delivery device defining a passage through which the pushrod is moved.

In another example, a surface (or wall) 380 of the housing and/or the pushrod can have a contact reducing surface profile that includes a plurality of discrete protrusions 382. In some embodiments, referring to FIGS. 6A and 6B, a surface 380 includes a plurality of cylindrical columns 382. Each column 382 extends from a base 381 of the surface 380. In a delivery device according to an embodiment described herein, in which a surface of the housing includes the plurality of cylindrical columns, at least one column from the plurality of columns is configured to contact a pushrod of the delivery device. In a similar manner, in a delivery device according to an embodiment described herein, in which a surface of the pushrod includes the plurality of cylindrical columns, at least one column is configured to contact a surface of the housing of the delivery device defining a passage through which the pushrod is moved.

Figure 7A:
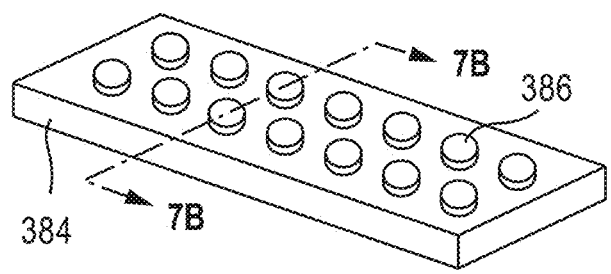
FIG. 7A is a perspective view of a surface geometry of a portion of a dosage delivery device according to an embodiment.
Figure 7B:
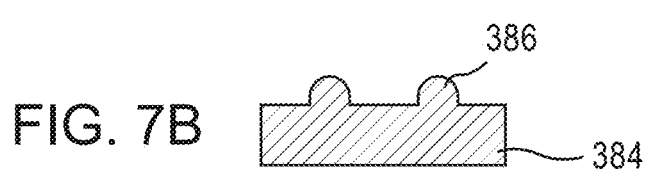
FIG. 7B is a cross-sectional view of a portion of the dosage delivery device shown in FIG. 7A taken along the line 7B-7B in FIG. 7A.
Figure 8:
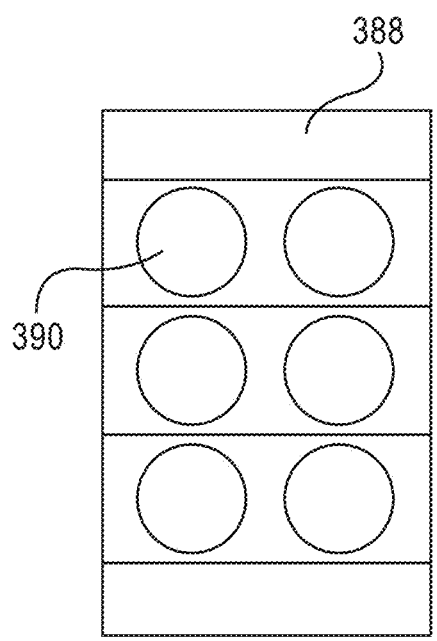
FIG. 8 is a top view of a surface geometry of a portion of a dosage delivery device according to an embodiment.
Figure 9:
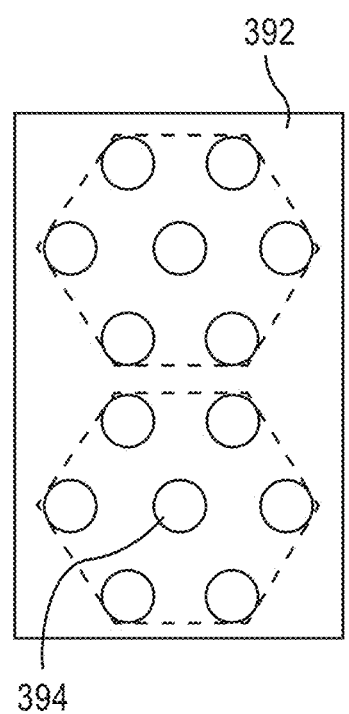
FIG. 9 is a top view of a surface geometry of a portion of a dosage delivery device according to an embodiment.

In some embodiments, referring to FIGS. 7A-7B, 8 and 9, a surface 384, 388, 392 includes hemispherical or generally convex projections or nubs 386, 390, 394, respectively, that can be arranged in a linear pattern (see, e.g., FIGS. 7A and 8), a hexagonal pattern (see, e.g., the phantom lines shown in FIG. 9), or other pattern. The nubs 386, 390, 394, arranged in the linear pattern are shown in FIG. 7A and FIG. 8 as being linearly arranged in two parallel rows that extend along a length of the surface 384, 388 (e.g., parallel to the direction of motion of the pushrod), however, in another embodiments, the nubs extended from a surface can be arranged in a single row, three rows, four rows, or more. In another embodiment, a surface can include nubs that are distributed or arranged on the surface in a random pattern. In each of the foregoing embodiments, in which the nubs are included on a surface of a housing of a delivery device, a distance between any two nubs is sufficiently short such that a pushrod of the delivery device cannot be lodged between or droop within the space between the two nubs as the pushrod is moved therethrough (e.g., during a dosage delivery event).

Figure 10A:
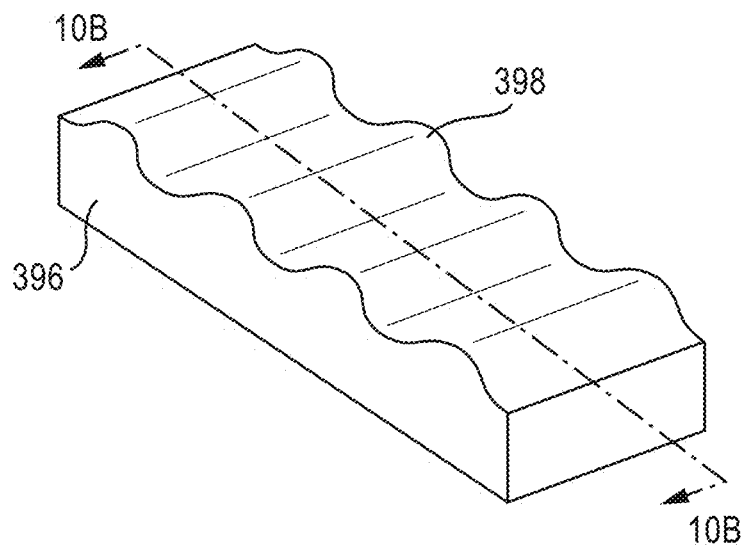
FIG. 10A is a perspective view of a surface geometry of a portion of a dosage delivery device according to an embodiment.
Figure 10B:
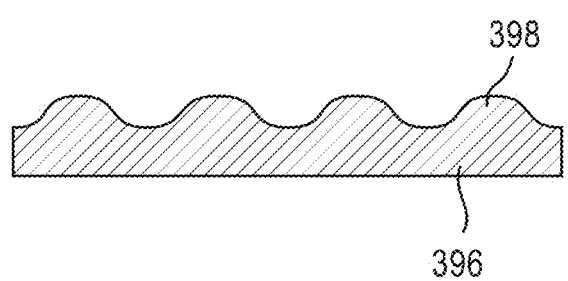
FIG. 10B is a cross-sectional view of a portion of the dosage delivery device shown in FIG. 10A taken along the line 10B-10B in FIG. 10A.

In yet another example, referring to FIGS. 10A-10B, a surface (or wall) 396 of a housing (not shown in FIGS. 10A-10B) and/or a pushrod (not shown in FIGS. 10A-10B) of a delivery device according to an embodiment herein can have a contact reducing surface profile that includes a plurality of waves 398 distributed along a length of the surface. In this manner, a cross-sectional profile of a length the surface, taken along line 10B-10B, has the shape of a sine wave or other suitable waveform shape, as shown in FIG. 10B.

Each of the non-planar (or contoured, textured, or the like) surface profiles described herein are configured to reduce the occurrence of and/or the magnitude of the frictional force and/or the change in the frictional force between the housing 310 and the pushrod 330, e.g., that results from contact therebetween during a dosage delivery event.

Figure 11:
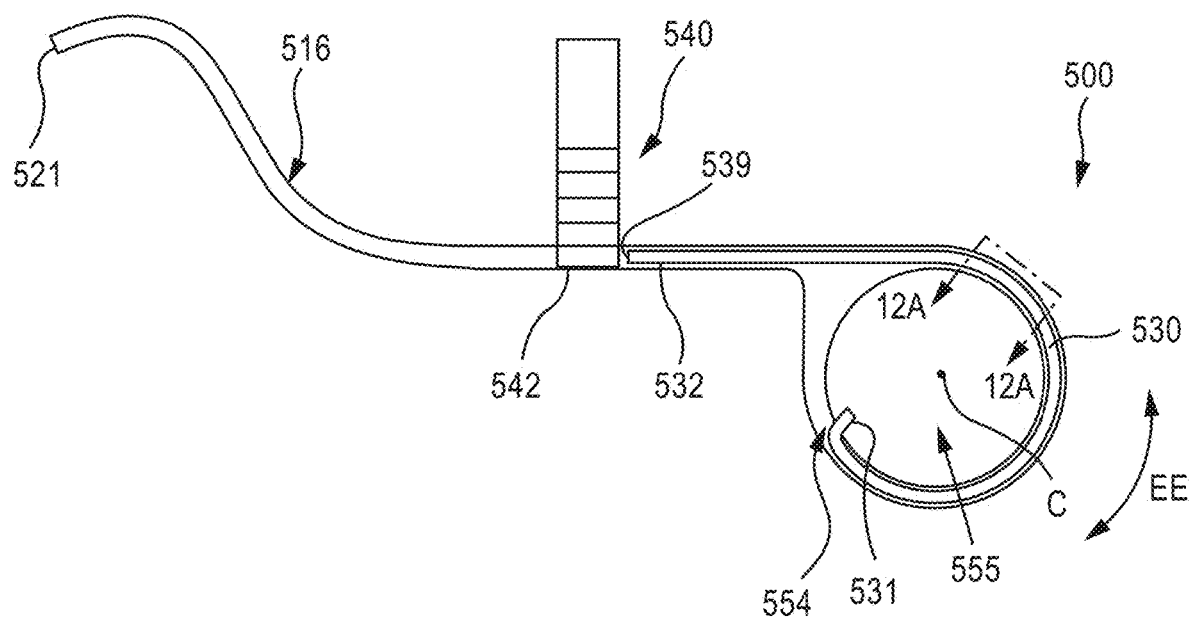
FIG. 11 is a schematic illustration of portions of a dosage delivery device according to an embodiment.

A dispensing device 500 according to an embodiment, portions of which are schematically illustrated in FIG. 11, includes a housing (not shown in FIG. 11) that defines a delivery passage 516 and a pushrod passage 554. The components or portions of the dispensing device 500 can be similar in many respects, or identical, to corresponding components or portions of the devices described herein, such as dosage delivery device 300, and thus are not described in detail with respect to device 500. The device 500 includes a pushrod 530 coupled to a rotating hub 555. It should be noted that the length of the pushrod 530 shown in FIG. 11 with respect to the length of the pushrod passage 554 and the delivery passage 516 is not to scale. For example, the pushrod 530 can have a length sufficient to permit the pushrod to be wrapped or wound around the hub 555 one, two, three or more times.

The hub 555, disposed within the housing of the device, is configured to rotate about a central axis C in a first direction and a second direction, represented by arrow EE in FIG. 11. Rotation of the hub 555 in the first direction moves at least a portion of the pushrod 530 in a curvilinear manner within the pushrod passage 554 and/or the delivery passage 516.

Figure 12A:
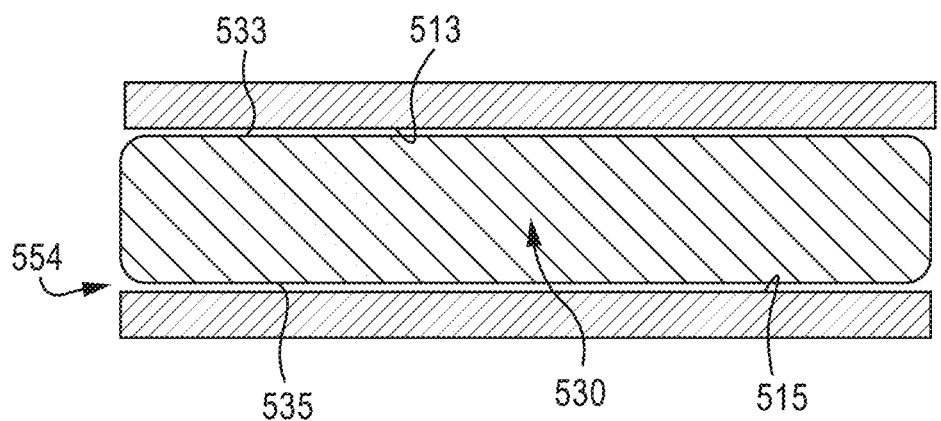
FIGS. 12A-12E are cross-sectional views of portions of either a surface area of a pushrod of a dosage delivery device or a surface area defining a hub volume of the dosage delivery device, showing surface geometries according to various embodiments.
Figure 12B:
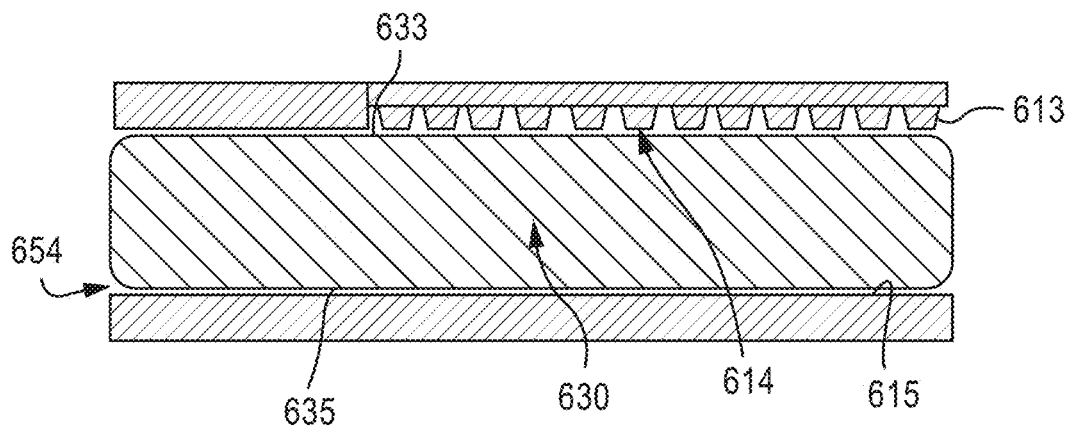
Figure 12C:
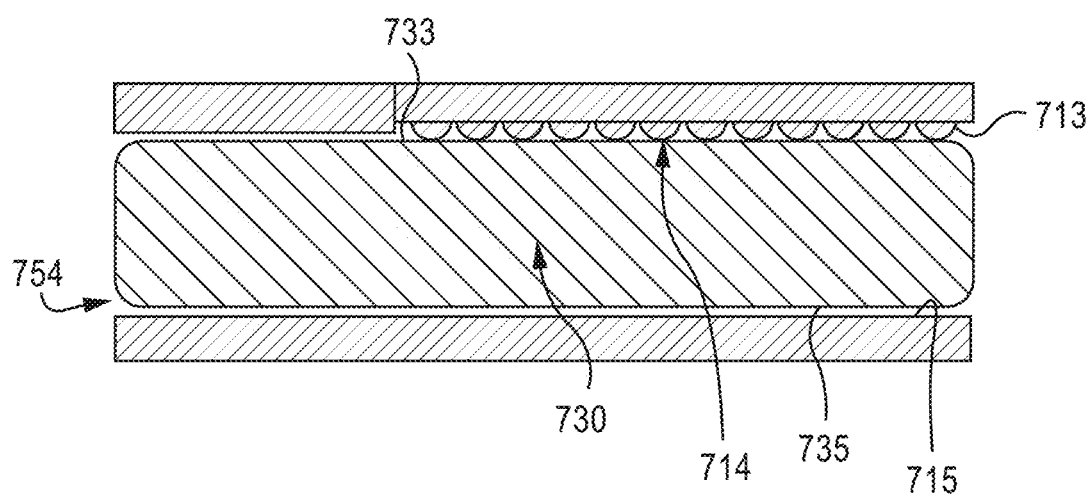

A surface of the pushrod 530, such as a surface of a portion of the pushrod that is moved through the pushrod passage 554, can be configured to contact a surface of a portion of the housing defining the pushrod passage 554 and/or the delivery passage 516 when the hub 555 moves the pushrod 530 within the pushrod passage 554 and/or the delivery passage 516. In some embodiments, for example, the pushrod 530 includes a first surface 513 and a second surface 515 opposite the first surface. Referring to FIG. 12A, which shows a cross-sectional profile of the pushrod 530 taken along line 12A-12A disposed within the pushrod passage 554, each of the first surface 533 and the second surface 535 of the pushrod 530 can be substantially planar, at least across a width of the pushrod that is shorter than its length. In some embodiments, the first surface 533 and/or the second surface 535 of the pushrod 530 is substantially smooth along a length and/or a width of the respective pushrod surface.

The portion of the housing defining the pushrod passage 554 includes a first surface 513 and a second surface 515 different from the first surface. The first surface 513 is proximate to the first surface 533 of the pushrod 530 when at least a portion of the pushrod is disposed within the pushrod passage 554. The second surface 515 is proximate to the second surface 535 of the pushrod 530 when the portion of the pushrod is disposed within the pushrod passage 554. Said another way, the first surface 533 of the pushrod 530 faces the first surface 513 of the portion of the housing defining the pushrod passage 554, and the second surface 535 of the pushrod 530 faces the second surface 515 of the portion of the housing defining the pushrod passage 554.

Referring again to FIG. 6A, each of the first surface 513 and the second surface 515 of the portion of the housing defining the pushrod passage 554 can be substantially planar, at least across a width of the pushrod passage that is shorter than its length. In some embodiments, the first surface 513 and/or the second surface 515 of the pushrod passage 554 is substantially smooth along a length and/or a width of the respective pushrod passage surface. In this manner, the pushrod 530 and the portion of the housing defining the pushrod can be characterized as being substantially flat and parallel to each other.

Figure 6A:
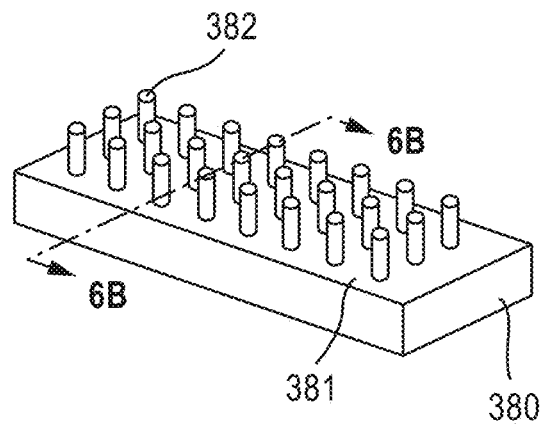
FIG. 6A is a perspective view of a surface geometry of a portion of a dosage delivery device according to an embodiment.

Although the surfaces 533, 535 of the pushrod 530 are shown in FIG. 6A for the purpose of clarity of illustration as being spaced apart, or not contacting, the surfaces 513, 515, respectively, of the housing, at least one of the surfaces 533, 535 of the pushrod 530 can be engaged with or contact at least one of the surfaces 513, 515, respectively, of the housing defining the pushrod passage 554, such as during movement of the pushrod 530 through the pushrod passage 554.

Because contact between portions of at least one of such planar surfaces 533, 535 of the pushrod 530 and such planar surfaces of the pushrod passage 554 can cause frictional forces that affect the substantially uniform and/or repeatable movement of the pushrod 530 during a drug dosage form delivery event (e.g., an actuation of the device) or during a subsequent drug dosage form delivery event, such as described with respect to dosage delivery devices herein (e.g., device 100, 300), in some embodiments, at least one of the pushrod 530 or the portion of the housing defining the pushrod passage 554 has a surface configured to reduce the occurrence, magnitude and/or direction of such frictional forces as compared to those that may occur if the pushrod and housing have flat, parallel surfaces, as shown and described with respect to FIG. 6A.

For example, at least a portion of the housing defining the pushrod passage 554 can have a nonplanar surface. More specifically, in some embodiments, at least a portion of the housing defining the pushrod passage 554 can have a surface that has a contour, texture, a raised and/or recessed geometrical surface pattern, and/or other physical characteristic that has the effect of making the surface nonplanar.

Figure 6B:
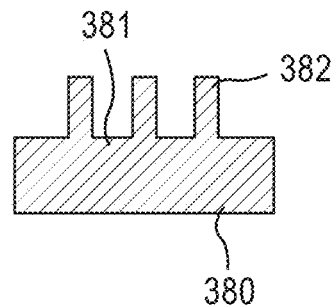
FIG. 6B is a cross-sectional view of a portion of the dosage delivery device shown in FIG. 6A taken along the line 6B-6B in FIG. 6A.

In some embodiments, a portion of a housing defining a pushrod passage 654 includes a first surface (or wall, such as a wall facing inwardly towards the hub 555) 613 having a plurality of teeth 614 extended therefrom. In this manner, the surface 613 of the portion of the housing defining the pushrod passage 654 can be characterized as having a toothed profile 6008, as shown in FIG. 6B. The teeth 614 can be similar in many respects to the plurality of teeth shown and described with respect to FIGS. 5A and/or 5B. At least one tooth can 614 be configured to engage or contact the pushrod 530. One or more teeth 614 can each include angled side wall portions and a substantially flat apex portion. The angled side wall of the tooth helps to prevent or reduce friction that may otherwise occur when a pushrod 630 engages the tooth of the surface 613.

The portion of the housing defining the pushrod passage 654 includes a second surface (or wall, such as a wall facing outwardly away from the hub) 615 that is substantially planar. In another embodiment, the second surface 615 of the portion of the housing can have toothed profile 614 similar to the first surface 613, or may have another contact reducing surface profile. In some embodiments, the toothed profile 614 can extend from a proximal end of the pushrod passage 654 up to, but not beyond, a cartridge receiving portion of the device defined by the housing. For example, the surface of the portion of the housing defining the pushrod passage can have the toothed profile 614 extend along the entire length of the pushrod passage 654. In other embodiments, the toothed profile can extend along less than the entire length of the pushrod passage 654.

In another example, in some embodiments, a portion of the housing defining the pushrod passage 754 includes a first surface (or wall, such as a wall facing inwardly towards the hub 555) 713 having a plurality of rounded protrusions or "bumps" 714 extended therefrom. The rounded protrusions 714 can be similar in many respects to the plurality of nubs shown and described with respect to FIGS. 7A-7B, 8 and/or 9. At least one rounded protrusion 714 can be configured to engage or contact the pushrod 530. The rounded end of the protrusion 714 is configured to reduce friction that may otherwise occur when the pushrod 730 engages the protrusion.

The portion of the housing defining the pushrod passage 754 includes a second surface (or wall, such as a wall facing outwardly away from the hub) 715 that is substantially planar. In another embodiment, the second surface 715 of the portion of the housing can have rounded protrusions 714 similar to those of the first surface 713, or may have another contact reducing surface profile. In some embodiments, the rounded protrusions 714 can extend from a proximal end of the pushrod passage 754 up to, but not beyond, a cartridge-receiving portion of the device defined by the housing. For example, the surface of the portion of the housing defining the pushrod passage 754 can include a plurality of rounded protrusions that extends along the entire length of the pushrod passage. In other embodiments, the plurality of rounded protrusions can extend along less than the entire length of the pushrod passage 754.

In another example, at least a portion of the pushrod of a delivery device can have a nonplanar surface. More specifically, in some embodiments, at least a portion of the pushrod can have a surface that has a contour, texture, a raised and/or recessed geometrical surface pattern, and/or other physical characteristic that has the effect of making the surface nonplanar. Said another way, in some embodiments, the reduction in the contact surface between the pushrod and the walls of the pushrod passage can be achieved by a surface profile of the pushrod.

Figure 12D:
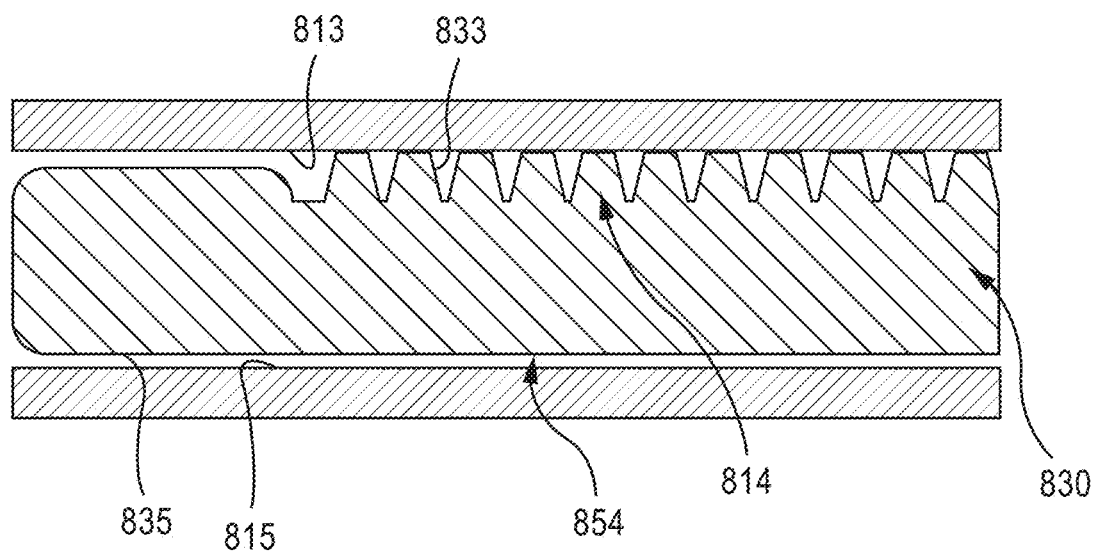

In some embodiments, as shown in FIG. 12D, a portion of the pushrod 830 includes a first (or upper or outwardly facing) surface 833 having a plurality of teeth 814 extended therefrom. In this manner, the surface 813 of the portion of the pushrod 830 can be characterized as having a toothed profile, as shown in FIG. 12D. The teeth 814 can be similar in many respects to the plurality of teeth shown and described with respect to FIGS. 5A, 5B and/or 6B. At least one tooth can be configured to engage or contact a portion of the housing defining the pushrod passage 854, such as a first surface 813 of the portion of the housing. Each tooth can include angled side wall portions and a substantially flat apex portion. The angled side wall of the tooth helps to prevent or reduce friction that may otherwise occur when the tooth engages the first surface 813 of the portion of the housing.

The portion of the pushrod 830 includes a second (or lower or inwardly facing) surface 835 that is substantially planar. In another embodiment, the pushrod 830 can have a second surface 835 including a toothed profile similar to that of the first surface 833, or may have another contact reducing surface profile. In some embodiments, the toothed profile can extend from a proximal end portion of the pushrod 830, or a portion of the pushrod proximate to the proximal end portion, of the pushrod passage 854 to a location along a length of the pushrod. In some embodiments, the toothed profile portion of the pushrod surface extends from a location on the pushrod close to the proximal end portion of the pushrod to a location along a length of the pushrod that does not travel, or is not moved, past the opening in the cartridge.

Figure 12E:
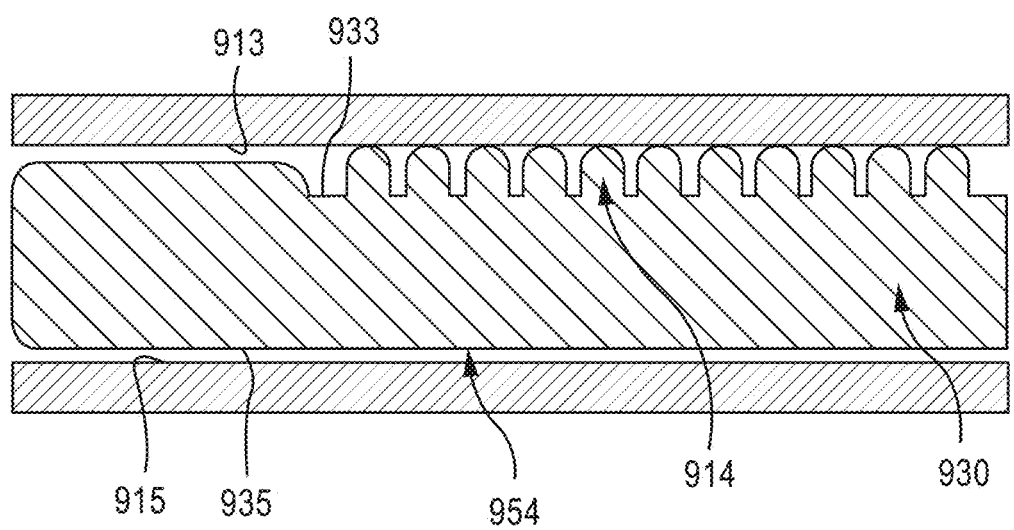

In some embodiments, as shown in FIG. 12E, a portion of the pushrod 930 includes a first (or upper or outwardly facing) surface 933 having a plurality of rounded protrusions or "bumps" 914 extended therefrom. The rounded protrusions 914 can be similar in many respects to the plurality of nubs shown and described with respect to FIGS. 7A-7B, 8, 9 and/or 6C. At least one rounded protrusion can be configured to engage or contact a portion of the housing defining the pushrod passage 954, such as a first surface 913 of the portion of the housing. The rounded end of the protrusion is configured to prevent or reduce friction that may otherwise occur when the protrusion 914 engages the first surface 913 of the portion of the housing.

The portion of the pushrod 930 includes a second (or lower or inwardly facing) surface 935 that is substantially planar. In another embodiment, the pushrod 930 can have a second surface including rounded protrusions 914 similar to those of the first surface 933, or may have another contact reducing surface profile. In some embodiments, the rounded protrusions 914 can extend from a proximal end portion of the pushrod 930, or a portion of the pushrod proximate to the proximal end portion, to a location along a length of the pushrod between its proximal end portion and its distal end portion. In some embodiments, the rounded protrusion of the pushrod surface extend from a location on the pushrod close to the proximal end portion of the pushrod to a location along a length of the pushrod that does not travel, or is not moved, past the opening in the cartridge.

Referring again to FIG. 11, the dosage delivery device 500 is configured to receive a cartridge 540 containing a series or stack of drug dosage forms 542. Although shown as being a "top feed" cartridge arrangement, in which the dosage form 542 moves vertically in a downward direction to enter a delivery passage 516 of the device, in other embodiments, the cartridge can be coupled to a housing of the device in a different manner, such as that shown and described herein with respect to FIG. 4 and device 300. A distal end portion 532 of the pushrod 530 is configured to engage a dosage form 542 when the hub 555 moves in the first direction, and thus moves the pushrod in a first direction towards an exit port 521 of the delivery passage 516, such that the dosage form 542 can be conveyed through the exit port.

Although the surfaces of the portion of the housing defining the pushrod passage (e.g., passages 554, 654, 754, 854, 954) and of the pushrod (e.g., pushrod 530, 630, 730, 830, 930) have been shown and described with respect to FIGS. 6A-6E as being planar, having a toothed profile, or having a plurality of rounded protrusions, in other embodiments, the surfaces of the portion of the housing defining the pushrod passage and of the pushrod may include one or more different patterns, textures, or contours.

Although the surfaces of the portion of the housing defining the pushrod passage (e.g., passages 554, 654, 754, 854, 954) and of the pushrod (e.g., pushrod 530, 630, 730, 830, 930) have been shown and described with respect to FIGS. 6A-6E as having a certain length, in other embodiments, such profiles can be included at one or more different sections along the length of the housing portion or pushrod, respectively. Similarly stated, as described above (e.g., with reference to FIG. 2), the surface contours can vary spatially along the length (or width) of the passage surfaces and/or pushrod surfaces.

In some embodiments, both one or more surfaces of the housing defining the passage and one or more of the surfaces of the pushrod can include one or more surface contours (e.g., nonplanar surface contours) as described herein.

In one embodiment, the clearance between the a portion of the housing defining the passage and the pushrod is designed so as to be larger or greater in one section, or at a first location, of the passage and smaller in another section, or a second location, of the passage.

In another embodiment, the portion of the housing, or walls, defining the passage includes a mechanical feature that maintains the clearance between the walls of the passage and the pushrod.

In another embodiment, the coefficients of friction of the surface of the pushrod 530 and that of the surface of the passage are reduced through the use of approved lubricant coatings or the use of anti-friction coatings on one or more portions, or locations, of the passage surface and the pushrod surface that do not come into contact with the drug dosage form. The portions or locations where these coatings are applied are selected to reduce the likelihood of migration of the coatings onto the drug dosage form or the drug dispensing pathway.

FIGS. 13A and 13B show a pushrod 1030 according to an embodiment in a first (or "free" or "undeformed") configuration and a second (or "deformed" or "wrapped") configuration. In some embodiments, when the pushrod 1030 is in the first configuration, the pushrod 1030 includes a bend or non-linearity 1033 in the proximal end portion 1031 thereof. Said another way, the proximal end portion 1031 of the pushrod 1030 forms an angle A of less than 180 degrees when the pushrod is in its first configuration. More particularly, the proximal end portion 1031 of the pushrod 1030 forms an angle at the intersection of a first portion $L_{A1}$ of a longitudinal axis of the proximal end portion and a second portion $L_{A2}$ of the longitudinal axis of the proximal end portion that is less than 180 degrees. Similarly stated, angle of less than 180 degrees is defined by an intersection of a longitudinal axis of a first portion of the proximal end portion 1031 of the pushrod 1030 and a longitudinal axis of a second portion of the proximal end portion of the pushrod 1030 the pushrod 1030 is in the first configuration.

When the pushrod 1030 is in the second (or deformed) configuration, the proximal end portion 1031 of the pushrod 1030 is coupled to an actuator hub 1055, and is in a coiled or wound or wrapped state such that a distal end surface (or "distal tip") 1039 of a distal end portion 1032 of the pushrod 1030 is disposed proximally to, and not in contact with, a drug dosage form 1042. The bend 1033 in the pushrod 1030 is towards the proximal end portion 1031 of the pushrod 1030, which is operatively connected to the actuator hub 1055.

In use, the pushrod 1030 may be wrapped and unwrapped more than a hundred times about the actuator hub 1055 as a result of repeated actuations of a delivery device. The bend 1033 can reduce potential part "drift" or plastic deformation, fatigue and wear over time. In particular, the pushrod 1030 including the bend portion 1033 retains its stiffness and form for a longer period of time than a pushrod that does not have a pre-machined or fabricated bend. The bend 1033 may act as a damped coil spring such that deformation forces are absorbed and released by the bend 1033 during the operation of the pushrod 1030 and as a result, the pushrod 1030 retains its form over a longer period of time.

Including the bend 1033 in the pushrod 1030 also reduces contact during use between the pushrod 1030 and the surfaces or walls of the housing defining a passageway through which at least a portion of the pushrod is moved, such as a pushrod passage 1054 defined about the actuator hub 1055 or a delivery passage 1016 defined by a proboscis portion 1020. With the addition of a bend 1033 in the pushrod 1030, the profile of the unwound section of the pushrod 1030 can be designed to reduce contact with the surfaces or walls of the housing defining the passageway, which results in lower frictional forces. Since frictional forces encountered by the pushrod 1030 must be overcome by the drive system, if the pushrod 1030 makes less contact with the walls of the housing defining the passageway there will be less friction and hence a smoother and more predictable motion of the pushrod 1030, as described herein (e.g., with respect to dosage delivery devices 100, 300 shown and described herein). The smoother motion will in turn give rise to more consistent sensor readings and fewer fault conditions. The bend location and bend angle are two parameters that can be optimized to reduce the angle at which the pushrod 1030 comes in contact with certain sections of the passageway as well as the locations where the pushrod 1030 comes in contact with the walls of the passageway, both of which are determinants of the frictional forces encountered by the pushrod 1030 during the drug-dispensing and calibration cycles.

The bend 1033 in the pushrod 1030 may be formed so that the included angle A is more than 90 degrees. Preferably, the included angle A may be between 120 and 150 degrees. In some embodiments, the pushrod 1030 is made of plastic and the bend 1033 may be set during the molding process, or alternatively it may be introduced during a heat-treatment step after molding. In other embodiments, where the pushrod 1030 is fabricated from a metal, the bend 1033 may be introduced during a stamping step or a similar machining process that deforms the material into the desired shape. The pushrod 1030 may be annealed or heat-treated after this step to relieve machining stress.

Although the bend 1033 is described as an angle A, in other embodiments, the bend 1033 in the proximal end portion of the pushrod 1030 can be a curved portion. Said another way, the proximal end portion of the pushrod 1030 can define a radius of curvature. Similarly stated, the bend portion 1033 may be characterized by a longitudinal axis of the pushrod 1030 defining an arc with a radius of curvature. In some embodiments, the pushrod 1030 can have a bend portion that has a radius of curvature of less than the length of the pushrod 1030. In other embodiments, the radius of curvature can be between about 1 times the length and about 3 times the length of the pushrod 1030. In other embodiments, the bend portion can have a radius of curvature that is between about 0.2 times the length of the pushrod and 0.7 times the length of the pushrod 1030.

In another embodiment, the pushrod 1030 may be made by welding or joining two sections at an angle where each section is made of the same material. In one embodiment, the pushrod 1030 may be fabricated by joining dissimilar materials. In another embodiment, one material may be selected for its suitability in contacting the drug dosage form while the other material may be selected for its suitability in maintaining its shape and form over hundreds of thousands of cycles of operation. In another embodiment, the material for one section of the pushrod 1030 may be selected for its anti-friction properties, while the material for the other section making up the pushrod 1030 may be selected for its stiffness or anti-wear properties.

The embodiments described herein can be used with any suitable drug dosage form, including, for example, sufentanil compositions. Such sufentanil compositions can include any of the compositions described in the '308 patent. In other embodiments, however, the devices and methods described herein can be used to deliver any other drug composition.

The embodiments described herein can be formed or constructed of one or more biocompatible materials. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof. A polymer material may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes, and/or blends and copolymers thereof. Examples of non-biodegradable polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, and/or blends and copolymers thereof.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having any combination or sub-combination of any features and/or components from any of the embodiments described herein. For example, although the pushrod 230 is shown as including a contoured distal end surface 239, in other embodiments, the pushrod 230 can include a squared, tapered, and/or convex distal end surface.

The specific configurations of the various components described herein can also be varied. For example, the size and specific shape of the various components can be different from the embodiments shown, while still providing the functions as described herein. Additionally, the relative size of various components of the devices shown and described herein with respect to the size of other components of the devices are not necessarily to scale.

Although the systems and methods are shown and described herein as providing for delivery of drug dosage forms to the oral mucosa, in other embodiments, the systems and the methods described herein can be applicable for delivery of any suitable therapeutic substance to any portion of the anatomy.

Although the devices and systems and methods are shown and described herein as providing for delivery of multiple drug dosage forms (e.g., from a cartridge), in other embodiments, any of the pushrods, housing or other components can be used in conjunction with a single-dose delivery device, such as those described in U.S. Pat. No. 8,548,623, entitled "Storage and Dispensing Devices for Administration of Oral Transmucosal Dosage Forms," which is incorporated herein by reference in its entirety.

In some embodiments, the pushrods and/or housing designs described herein can be used in either an actual drug delivery device or a simulated drug delivery device. A simulated drug delivery device can, for example, correspond to an actual drug delivery device and can be used, for example, to train a user in the operation of the corresponding actual medicament delivery device. Such simulated device can be devoid of actual drug-containing dosage forms.

Similarly, where methods and/or events described above indicate certain events and/or procedures occurring in certain order, the ordering of certain events and/or procedures may be modified. While the embodiments have been particularly shown and described, it will be understood that various changes in form and details may be made.

What is claimed is:

1. An apparatus, comprising:
   a housing defining a passage and an exit port in fluid communication with the passage, the passage having a predefined curved shape along a length thereof;
   an actuator hub rotatably disposed within a hub volume defined by the housing; and
   a pushrod coupled to the actuator hub and having a proximal end portion and a distal end portion, the distal end portion of the pushrod movable from a first position within the passage to a second position to move a drug dosage form through at least a portion of the passage to convey the drug dosage form through the exit port, a portion of the pushrod including the proximal end portion being wound about the actuator hub when the distal end portion of the pushrod is in the first position, the proximal end portion of the pushrod having a prefabricated bend of less than 180 degrees that dampens a deformation force produced during rotation of the actuator hub to move the distal end portion of the pushrod from the first position to the second position,
   a surface of the housing defining the predefined curved shape of the passage having a contact-reducing surface profile configured to substantially prevent negative acceleration of the distal end portion of the pushrod within the passage due to frictional contact between the pushrod and the housing during movement of the distal end portion of the pushrod from its first position to its second position.

2. The apparatus of claim 1, wherein a surface of the pushrod is configured to be in sliding contact with the surface of the housing when the distal end portion of the pushrod is moved from the first position to the second position.

3. The apparatus of claim 1, wherein the passage is disposed about at least a portion of the hub volume, the surface of the housing defining the passage disposed about the hub volume has the contact-reducing surface profile.

4. The apparatus of claim 1, wherein the contact-reducing surface profile is configured such that a first portion of the surface contacts the drug dosage form when the distal end portion of the pushrod is moved from its first position to its second position and such that the drug dosage form does not contact a second portion of the surface of housing defining the passage when the distal end portion of the pushrod is moved from its first position to its second position.

5. The apparatus of claim 1, wherein:
   a surface of the pushrod is in sliding contact with the contact-reducing surface profile of the surface of the housing when the distal end portion of the pushrod is moved from the first position to the second position, and
   the contact reducing surface profile includes a plurality of protrusions.

6. The apparatus of claim 1, wherein:
   the pushrod is flexible to assume the predefined curved shape of the passage when the distal end portion of the pushrod is moved from the first position to the second position.

7. The apparatus of claim 1, wherein the pushrod defines an opening configured to be detected by a sensor when the pushrod is moved within the passage.

8. The apparatus of claim 1, wherein a first portion of the pushrod is transparent to a sensor, a second portion of the pushrod different from the first portion is opaque to the sensor.

9. The apparatus of claim 1, wherein a cross-section of the contact-reducing surface profile, taken in the direction of a longitudinal axis of one of the pushrod or the passage, has a waveform shape.

10. The apparatus of claim 1, wherein a portion of a surface of the push rod configured to contact the contact-reducing surface profile of the surface of the housing is planar.

11. The apparatus of claim 1, wherein a surface of the pushrod is configured to be in sliding contact with the surface of the housing defining the passage when the distal end portion of the pushrod is moved from its first position to its second position within the passage, the contact-reducing surface profile defines a geometric pattern that repeats along at least one of a length or a width of the surface.

12. The apparatus of claim 1, wherein a surface of the pushrod is in sliding contact with the surface of the housing defining the passage when the distal end portion of the pushrod is moved from its first position to its second position within the passage, the contact-reducing surface profile defining a random geometric pattern.

13. The apparatus of claim 1, further comprising:
   the drug dosage form, the drug dosage form including sufentanil.

14. The apparatus of claim 1, wherein:
   a surface of the pushrod is in sliding contact with the contact-reducing surface profile of the surface of the housing when the distal end portion of the pushrod is moved from the first position to the second position, and
   the contact-reducing surface profile defines a plurality of grooves.

15. The apparatus of claim 14, wherein each groove from the plurality of grooves is parallel to another groove from the plurality of grooves.

16. The apparatus of claim 14, wherein a groove from the plurality of grooves has an elongate axis that is transverse to a direction defined by the movement of the pushrod from its first position to its second position.

17. The apparatus of claim 14, wherein at least one groove from the plurality of grooves defines a "V"-shape, a chevron shape, and/or herringbone shape, with the vertices of the grooves aligned with a direction of motion of the pushrod.

18. An apparatus, comprising:
a housing defining a delivery passage and an exit port in fluid communication with the delivery passage, the housing defining a hub volume within which a hub is rotatably disposed; and
a pushrod, a distal end portion of the pushrod being movably disposed in the delivery passage to convey a drug dosage form through the exit port when the distal end portion of the pushrod is moved from a first position to a second position, a proximal end portion of the pushrod coupled to the hub such that rotation of the hub and the proximal end portion of the pushrod causes the distal end portion of the pushrod to move between the first position and the second position,
a surface of the housing defining the hub volume having a contact-reducing surface profile,
a portion of the pushrod movably disposed within the hub volume contacts the contact-reducing surface profile of the surface of the housing defining the hub volume when the pushrod is moved from the first position to the second position, the proximal end portion of the pushrod being disposed within the hub volume and having a prefabricated bend of less than 180 degrees, the prefabricated bend reduces contact of the portion of the pushrod with the contact reducing surface profile of the surface of the housing defining the hub volume.

19. The apparatus of claim 18, further comprising:
the drug dosage form, the drug dosage form including sufentanil.

20. An apparatus, comprising:
an actuator hub; and
a pushrod, a distal end portion of the pushrod configured to be movably disposed within a delivery passage of a drug delivery device to convey a drug dosage form through the delivery passage when the distal end portion of the pushrod is moved from a first position to a second position, a portion of the pushrod coupled to and wrapped around the actuator hub when the pushrod is in its first position, the portion of the pushrod being unwrapped from around the actuator hub in response to rotation of the actuator hub to move the distal end portion of the pushrod from the first position to the second position,
the proximal end portion of the pushrod having a prefabricated angle of less than 180 degrees, the prefabricated angle of the pushrod being disposed between the portion of the pushrod wrapped around the actuator hub when the pushrod is in its first position and an end of the pushrod inserted into the actuator hub.

21. The apparatus of claim 20, wherein:
the delivery passage has a curved shape; and
at least a portion of the pushrod is flexible to assume the curved shape of the delivery passage when the distal end portion of the pushrod is moved from the first position to the second position.

22. The apparatus of claim 20, further comprising:
the drug dosage form, the drug dosage form including sufentanil.

23. The apparatus of claim 20, wherein the angle is molded, stamped, or formed by heat-treatment.

24. The apparatus of claim 20, wherein the angle is defined by an intersection of a first portion of a longitudinal axis of the proximal end portion of the pushrod when the pushrod is in an undeformed configuration, and a second portion of the longitudinal axis of the proximal end portion of the pushrod when the pushrod is in the undeformed configuration.

25. The apparatus of claim 24, wherein the angle is between 90 degrees and 180 degrees.

26. The apparatus of claim 24, wherein the angle is between 120 degrees and 150 degrees.

* * * * *

UNITED STATES PATENT AND TRADEMARK OFFICE
CERTIFICATE OF CORRECTION

| | | |
|---|---|---|
| PATENT NO. | : 11,058,856 B2 | Page 1 of 1 |
| APPLICATION NO. | : 14/978634 | |
| DATED | : July 13, 2021 | |
| INVENTOR(S) | : Chiu et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 768 days.

Signed and Sealed this
Thirteenth Day of December, 2022

*Katherine Kelly Vidal*

Katherine Kelly Vidal
*Director of the United States Patent and Trademark Office*